(12) United States Patent
Pavey et al.

(10) Patent No.: US 10,324,024 B2
(45) Date of Patent: Jun. 18, 2019

(54) METHODS AND SYSTEMS FOR CHEMICAL VAPOUR SENSING

(71) Applicant: THE COMMONWEALTH OF AUSTRALIA, Edinburgh (AU)

(72) Inventors: Karl David Pavey, Newport (AU); Nicholas John Fitzgerald, Northcote (AU); Craig Jason Stevens, Northcote (AU); John Thomas Huberts, Stretton (AU); Anthony Andrew Pahl, McKinnon (AU); Igor Henricus Van de Griendt, Essendon North (AU)

(73) Assignee: THE COMMONWEALTH OF AUSTRALIA, Fishermans Bend (AU)

( * ) Notice: Subject to any disclaimer, the term of this patent is extended or adjusted under 35 U.S.C. 154(b) by 0 days.

(21) Appl. No.: 15/507,170

(22) PCT Filed: Aug. 27, 2014

(86) PCT No.: PCT/AU2014/000851
§ 371 (c)(1),
(2) Date: Feb. 27, 2017

(87) PCT Pub. No.: WO2016/029237
PCT Pub. Date: Mar. 3, 2016

(65) Prior Publication Data
US 2017/0248514 A1  Aug. 31, 2017

(51) Int. Cl.
*G01N 21/05* (2006.01)
*G01D 18/00* (2006.01)
(Continued)

(52) U.S. Cl.
CPC ............. *G01N 21/05* (2013.01); *G01D 18/00* (2013.01); *G01N 21/783* (2013.01);
(Continued)

(58) Field of Classification Search
CPC ...... G01N 21/05; G01N 21/783; G01N 18/00; G01N 33/0022; G01N 33/0031;
(Continued)

(56) References Cited

U.S. PATENT DOCUMENTS 5,280,273 A   1/1994   Goldstein
6,085,576 A   7/2000   Sunshine et al.
(Continued)

FOREIGN PATENT DOCUMENTS

WO   2005/119180 A2   12/2005

OTHER PUBLICATIONS

International Search Report, dated Jun. 19, 2015, for PCT/AU2014/000851, 7 pages.
Written Opinion, dated Jun. 19, 2015, for PCT/AU2014/000851, 10 pages.

*Primary Examiner* — Hina F Ayub
(74) *Attorney, Agent, or Firm* — Seed IP Law Group LLP

(57) ABSTRACT

Embodiments relate generally to methods, systems, devices and applications for use in relation to the detection of chemical vapours. A particular embodiment relates to a device for chemical vapour sensing. The device comprises a housing of a size to be manually portable, the housing defining a plurality of receptors adapted to receive a respective plurality of manually replaceable chemical vapour sensing components. The device further comprises at least one signal receiver to receive data signals from each chemical vapour sensing component when the chemical vapour sensing component is positioned in one of the receptors.

8 Claims, 25 Drawing Sheets

(51) Int. Cl.
*G01N 21/78* (2006.01)
*G01N 33/00* (2006.01)
*G08B 17/113* (2006.01)
*G08B 21/14* (2006.01)
*G08B 25/08* (2006.01)

(52) U.S. Cl.
CPC ..... *G01N 33/0022* (2013.01); *G01N 33/0031* (2013.01); *G01N 33/0036* (2013.01); *G01N 33/0057* (2013.01); *G01N 33/0063* (2013.01); *G08B 17/113* (2013.01); *G08B 21/14* (2013.01); *G08B 25/08* (2013.01)

(58) Field of Classification Search
CPC .......... G01N 33/0036; G01N 33/0057; G01N 33/0063; G01N 17/113
USPC ......................................................... 356/246
See application file for complete search history.

(56) References Cited

U.S. PATENT DOCUMENTS

| | | | | |
|---|---|---|---|---|
| 6,471,136 B1* | 10/2002 | Chatterjee | ............ | F25D 17/042 237/2 B |
| 6,609,295 B1* | 8/2003 | Koyama | ............ | H05K 13/0473 29/566.3 |
| 7,542,138 B2* | 6/2009 | Gardner, Jr. | ............ | G01J 3/02 356/244 |
| 2004/0013571 A1* | 1/2004 | Morris | ............ | G01N 33/0031 422/94 |
| 2011/0064886 A1* | 3/2011 | Tsao | ............ | G01N 21/553 427/539 |
| 2012/0024042 A1 | 2/2012 | Vass et al. | | |
| 2012/0050606 A1* | 3/2012 | Debevec | ............ | G03B 15/07 348/370 |
| 2012/0103060 A1* | 5/2012 | Brasfield | ............ | G01N 33/0004 73/23.34 |

* cited by examiner

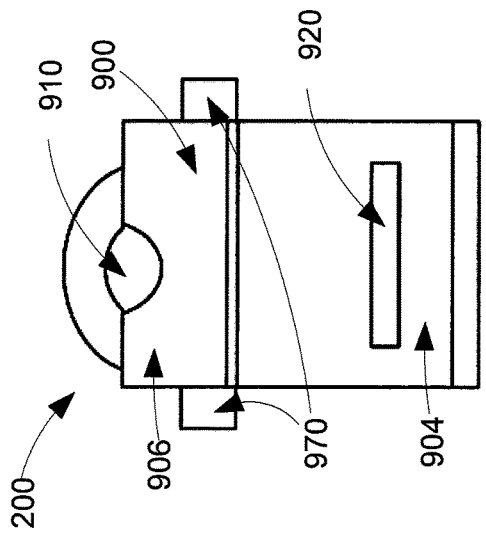
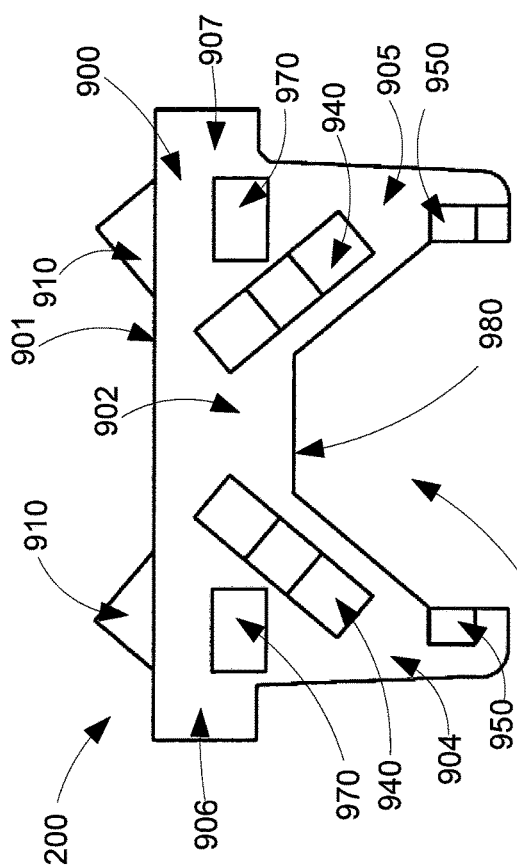
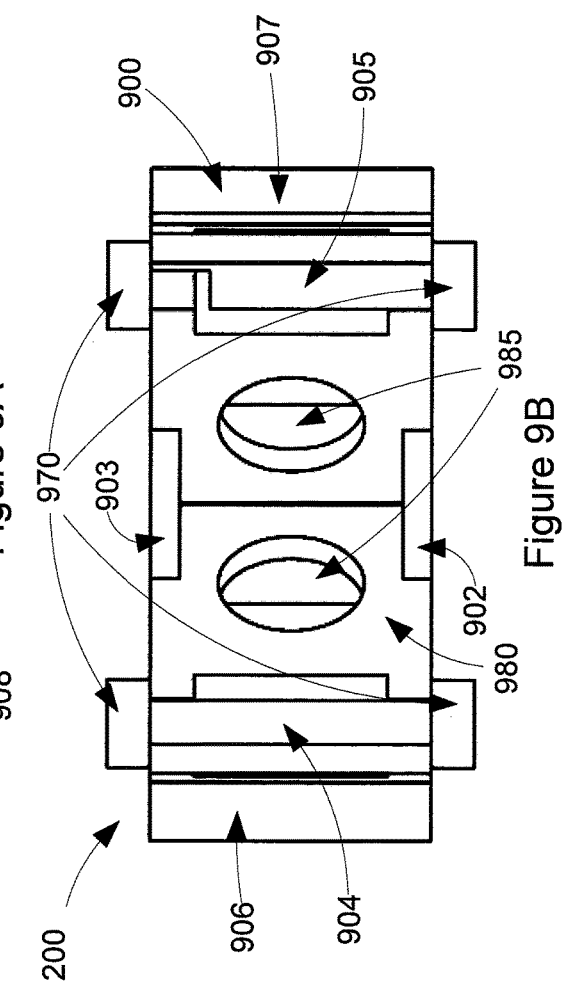
Figure 9C
Figure 9A
Figure 9B

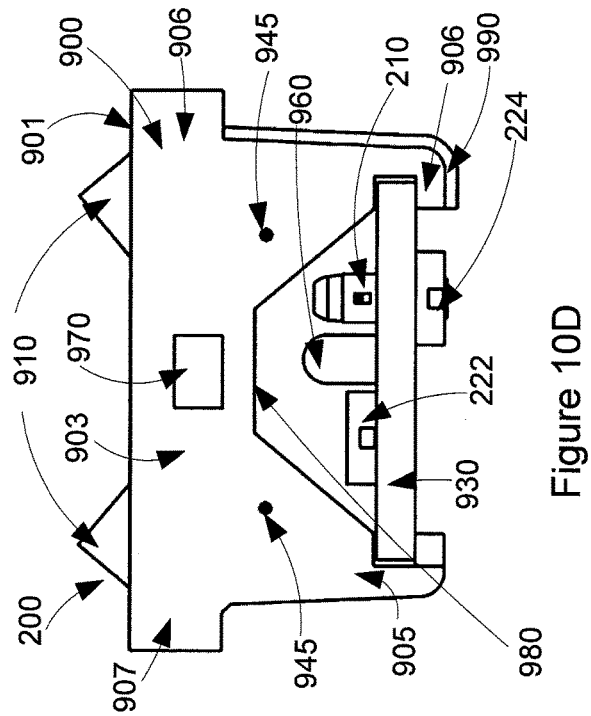
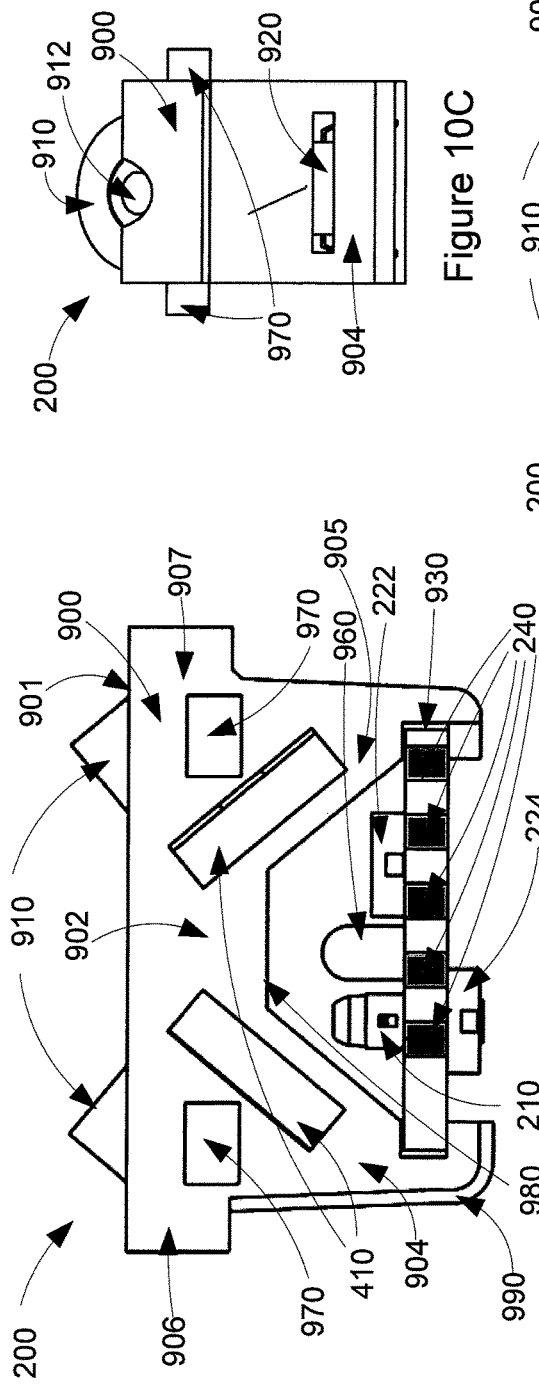
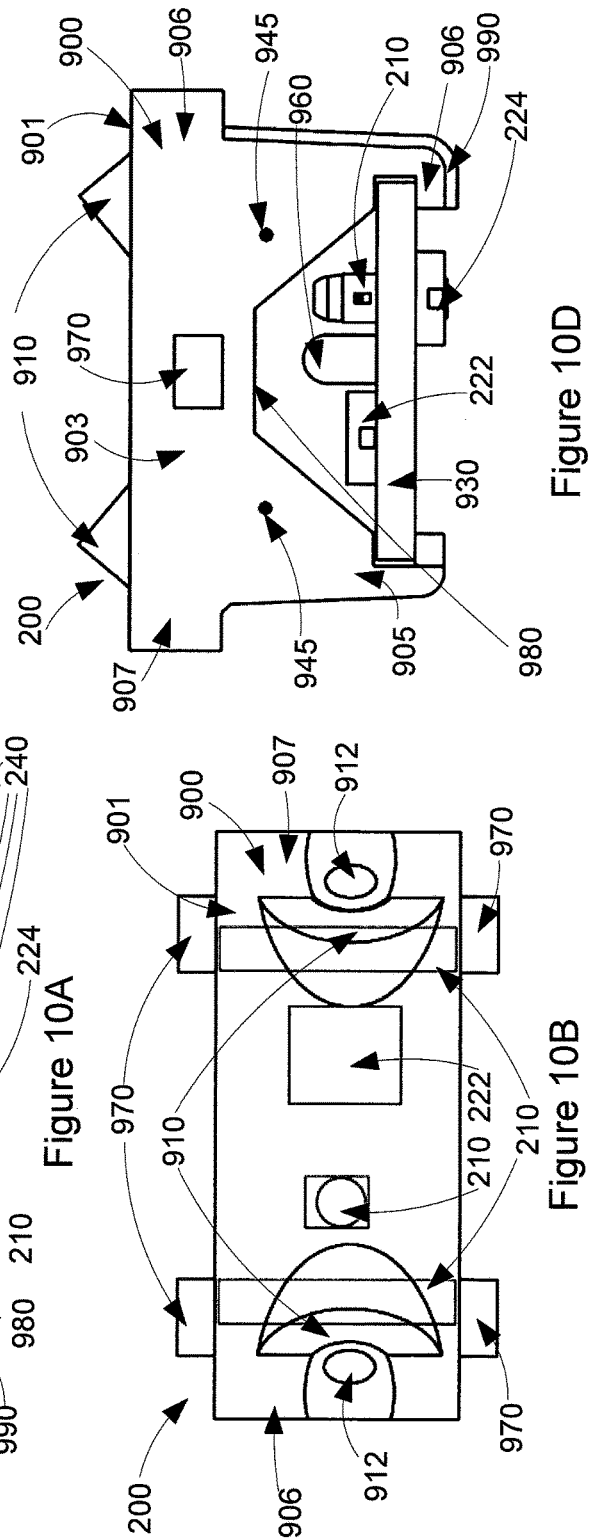

| | Target Gas | | | | | | | |
|---|---|---|---|---|---|---|---|---|
| | Ammonia | Chlorine | Hydrogen sulphide | Sulphur dioxide | Hydrogen cyanide | Nitrogen dioxide | Phosphine | Hydrochloric acid |
| Node Number | 1 | 2 | 3 | 4 | 5 | 6 | 7 | 8 |
| LED Specification | SSL-LXA228UGCCTR11 | SMC470 | SMC415 | SMC470 | SMC720 | RLCU-400 | SMC415 | SSL-LXA228USBCTR11 |
| Kohm ID value | 1 | 2.55 | 4.7 | 6.8 | 10 | 15 | 24 | 39 |
| Responding Nodes | | | | | | | | |
| Ammonia | ■ | | | | | | | |
| Chlorine | | ■ | | | | | | |
| Hydrogen sulphide | | | ■ | | | | | ■ |
| Sulphur dioxide | | | | ■ | | | | |
| Hydrogen cyanide | | | | | ■ | | | |
| Nitrogen dioxide | | ■ | | | | ■ | | |
| Phosphine | | | ■ | | | | ■ | |
| Hydrochloric acid | | | | | | | | ■ |

METHODS AND SYSTEMS FOR CHEMICAL VAPOUR SENSING

TECHNICAL FIELD

Described embodiments generally relate to methods, systems, devices and applications for use in relation to the detection of chemical vapours.

BACKGROUND

Detection of chemical vapours, such as toxic industrial chemical vapours and chemical warfare agent vapours, can be beneficial for the health and safety of factory workers at industrial sites as well as for emergency services and military personnel. Detection of these vapours can be used to warn and alert people so that they can clear a hazardous area, and/or seek appropriate medical attention where there has been a dangerous level of exposure.

Various forms of equipment exist for the detection of vapours, but many of these lack the sensitive, timely response and accuracy required to warn people of chemical threats. For example, large laboratory instruments can detect chemical vapours but rely on techniques such as gas and liquid chromatography. While these are sensitive and wide ranging in detection scope, these devices are large and difficult to transport. Furthermore, they often require appropriately trained staff to operate them, and often require significant setup time in the form of sample preparation.

An alternative technique is the use of laser based technologies to interrogate the atmosphere for chemical vapours at distances out to 4 to 5 km. These techniques are capable of identifying individual chemical species using infrared or raman techniques. However, the required instrumentation is not easily portable, and results can be affected by atmospheric conditions.

There are some portable devices for chemical vapour detection available. These may be miniaturised active electronic devices, which may include gas chromatographs, mass spectrometers, ion mobility spectrometers, flame photometers, photoionization detectors, infrared spectrometers and raman spectrometers, or passive devices which generally work on the principle of colour change chemistry.

The active devices are often prone to contamination, which can result in significant instrument down-time and may limit the functions of the device whilst the devices are in use. Active devices may also impart a logistical burden.

The passive devices generally have a lower logistical burden, being lightweight and portable, requiring no power and very limited user training, but can be insensitive, slow to react, and may require user intervention to sample based upon good colour vision and best judgement. False positives or negatives may occur as a result of the outputs being subjective to the user even with perfect colour vision. As a result, low but harmful levels of chemical vapour can go undetected or a false positive may be perceived.

It is desired to address or ameliorate one or more shortcomings or disadvantages associated with prior methods, systems, devices and applications for use in relation to the detection of chemical vapours, or to at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Some embodiments relate to a device for chemical vapour sensing, comprising:
- a housing of a size to be manually portable, the housing defining a plurality of receptors adapted to receive a respective plurality of manually replaceable chemical vapour sensing components; and
- at least one signal receiver to receive data signals from each chemical vapour sensing component when the chemical vapour sensing component is positioned in one of the receptors.

The housing may further define an air distribution plenum allowing for air to be distributed to each receptor. The plenum may comprise at least one filter to inhibit particulate matter from entering each receptor. The receptors may be positioned in an array around the plenum. The receptors may be positioned radially around the plenum. The air distribution plenum may allow for a substantially equal amount of air to be distributed to each receptor.

The device may further comprise a mechanism for forcing air through the plenum. The mechanism may comprises a fan in some embodiments. The mechanism may be configured to operate at a duty cycle of less than 100%.

The device may further comprise memory to store data received by the at least one signal receiver.

The device may further comprise a processor to receive the data signals from the at least one signal receiver. The device may further comprise a printed circuit board, the printed circuit board carrying the processor and the at least one signal receiver. The printed circuit board may comprise a protective coating.

The processor may be configured to monitor values indicated by the data signals and to determine that a first alarm condition has been met when the values reach a first predetermined threshold value. The processor may be further configured to analyse a rate of change of values indicated by the data signals and to determine that a second alarm condition has been met when the rate of change of the values reaches a second predetermined threshold value.

The processor may be configured to generate an alarm output when the first and second alarm conditions have been met. The device may further comprise indication components configured to be activated by the alarm output from the processor. The indication components may include at least one of an audible, visual or tactile indication component.

The processor may be configured to detect whether a sensing component is positioned in any one of the plurality of receptors. The processor may be further configured to receive identification data from a sensing component that is positioned in one of the receptors. The processor may further be configured to calibrate at least one setting of the sensing component.

The device may further comprise a communication component adapted to communicate with an external device. The communication component may be configured to communicate output data to the external device based on data signals received from any sensing components positioned in respective receptors. The output data may be communicated to the external device in substantially real time in response to receipt of the data signals from sensing components that are positioned in the receptors. Alternatively, the output data may be retrieved from data storage of the device.

The communication component may be adapted to communicate with the external device wirelessly. The communication component may be configured to switch to a low power mode when the communication component is not transmitting or receiving signals.

The device may further comprise at least one environmental sensor. The environmental sensor may comprise at least one of a temperature sensor and a humidity sensor. The device may be configured to use signals received from the environmental sensor to electronically filter data signals received from each sensing component that is positioned in one of the receptors.

Each receptor in the plurality of receptors may comprise a sensing component retention mechanism for holding the chemical vapour sensing component within the receptor.

The device may further comprise a power source. The power source may comprise a rechargeable battery in some embodiments.

The device may further comprise a cover to cover at least a part of the housing defining the receptors. The device may further comprise an attachment component for attaching the device to one of an article of clothing, a vehicle or a structure.

Each receptor may comprise an airflow restrictor to reduce airflow through the receptor when there is no sensing component positioned in the receptor. The airflow restrictor may reduce the airflow through the receptor to a level approximately equal to a level of airflow through the receptor that would occur when a chemical vapour sensing component is received in the receptor.

Each receptor may comprise a signal coupling portion to allow signals to be communicated from a chemical vapour sensing component positioned in the receptor to the at least one signal receiver. The signal coupling portion may comprise a set of electrical contacts.

The device may further comprise at least one of the chemical vapour sensing components received in a respective receptor.

Some embodiments may relate to a device for chemical vapour sensing, comprising:
 a housing of a size to be manually portable, the housing defining a plurality of receptors adapted to receive a respective plurality of manually replaceable chemical vapour sensing components, and the housing further defining an air distribution plenum allowing for air to be distributed to each receptor.

The device may further comprise a mechanism for forcing air through the plenum to distribute the air to each receptor.

Some embodiments may relate to a sensing component for sensing chemical vapours, comprising:
 a housing defining an airflow path, the housing further defining a complementary shaped structure configured to be received in a receptor of a carrier device;
 a first substrate positioned so that vapours flowing along the airflow path can contact the first substrate, wherein at least one property of the first substrate changes when it comes into contact with a target vapour;
 a sensing element, the element being configured to detect a change of the at least one property of the first substrate and to produce a signal based on the detected change; and
 a signal coupling portion to allow output of output signals based on the produced signal to the carrier device;
 wherein the sensing component is configured to be manually insertable into the receptor and manually removable from the receptor.

The component may further comprise a processor to receive the produced signal and generate the output signals.

The signal coupling portion may comprise a set of electrical contacts.

The component may further comprise a printed circuit board, the printed circuit board carrying the sensing element and the signal coupling portion.

The component may further comprise an airflow diversion member positioned in relation to the airflow path to induce air turbulence within the housing. The airflow diversion member may comprise a wall-like barrier. The airflow diversion member may be positioned to promote airflow towards the substrate.

The component may further comprise identification circuitry to allow the component to be identified electronically. The identification circuitry may comprise an electronic component having a predetermined value to act as an identifier of the sensing component.

The substrate may be configured to change in colour when it comes into contact with a target vapour.

The component may further comprise a light emitting component positioned to direct light toward the first substrate, and the sensing element may be positioned to receive light from the first substrate. The substrate may be positioned to reflect light from the light emitting component to the sensing element. Alternatively, the substrate may be positioned so that light transmitted from the light emitting component must pass through the substrate to be received at the sensing element.

The light emitting component may be tuneable to emit a pre-determined wavelength of light. The wavelength of the emitted light may be one of: inside the visible spectrum; and outside the visible spectrum. The light emitting component may comprise a broad spectrum light source. The light emitting component may comprise multiple light sources. The light emitting component may be configured to emit light at a duty cycle less than 100%.

The sensing element may comprise a photo-sensitive element. The photo-sensitive element may be tuneable to detect a pre-determined wavelength of light. The wavelength of the detected light may be one of: inside the visible spectrum; and outside the visible spectrum.

The component may further comprise a second substrate. The second substrate may be positioned to receive light reflected by the first substrate, and to reflect light towards the sensing element. The first substrate may be positioned at an angle of between 60 and 120° to the second substrate. The first substrate may be positioned at an angle of around 90° to the second substrate.

The light emitting member may be positioned at an angle of between 30 and 60° to the first substrate. The light emitting member may be positioned at an angle of around 45° to the first substrate.

The second substrate may be positioned at an angle of between 30 and 60° to the sensing element. The second substrate may be positioned at an angle of around 45° to the sensing element.

The component may further comprise a calibration element configured to receive light from the light emitting component and to produce an output based on the received light. The brightness of the light emitting component may be controlled based on the output of the calibration element.

At least one of the light emitting component and the sensing element may comprise a hydrophilic surface treatment. The hydrophilic surface treatment may comprise a superhydrophilic surface treatment. The hydrophilic surface treatment may comprise an oxygen plasma coating.

At least one of the light emitting component and the sensing element may comprise a superhydrophobic surface treatment.

The substrate may comprise a structural layer and a dopant. The structural layer may be saturated in the dopant.

The sensing element may comprise an array of sensing sub-elements. Each sensing sub-element may be tuned to detect a change of a property of a part of the first substrate. The sensing sub-elements may be each tuned to detect a change in intensity of different wavelengths of light received from the first substrate.

The first substrate may comprise an array of substrate sections. Each substrate section may be configured to react to a different chemical vapour.

The target vapour may be a vapour that is potentially harmful to human health.

The component may further comprise a human-readable label identifying the target vapour.

The housing may be configured to allow fluid communication between the airflow path and a separate airflow path defined by the carrier device. The component may further comprise a seal to reduce air loss between the housing and the carrier device.

A device according to some embodiments may further comprise the sensing component described above.

Some embodiments relate to a method for chemical vapour sensing, the method comprising:
monitoring a value of a property of a substrate, wherein the substrate is sensitive to the chemical vapour;
calculating a rate of change of the value over time;
determining an alarm condition when both the value and the rate of change of the value reach respective predetermined thresholds.

The method may further comprise storing identification data corresponding to a type of the substrate for which the alarm condition was determined.

The method may further comprise:
monitoring values of respective properties of a plurality of substrates, wherein the plurality of substrates are sensitive to different chemical vapours;
calculating rates of change of the values over time;
determining an alarm condition when, for one of the substrates, both the value and the rate of change of the value reach first and second predetermined thresholds.

The method may further comprise identifying when more than one of the values of the respective properties of the plurality of substrates and respective rates of change of the values of the respective properties of the plurality of substrates reach respective predetermined thresholds, and identifying a plurality of substrates that the values relate to.

The method may further comprise identifying the chemical vapour based on the identified substrates. The identifying may comprise comparing the identified substrates to a predetermined set of data. The predetermined set of data may comprise a lookup table.

Some embodiments may relate to a method comprising:
receiving air at a chemical vapour sensing device;
distributing the air to an array of receptors adapted to receive a respective plurality of manually replaceable chemical vapour sensing components;
receiving signals from at least one of the chemical vapour sensing components;
determining an alarm condition based on the signals received from the at least one chemical vapour sensing component.

Some embodiments may relate to a kit comprising a device according to some embodiments and a sensing component according to some embodiments.

BRIEF DESCRIPTION OF DRAWINGS

Embodiments are described in further detail below, by way of example and with reference to the accompanying drawings, in which:

FIG. 9A is a front view of a sensing node from FIG. 3;

FIG. 9B is a bottom view of a sensing node from FIG. 3;

FIG. 9C is a side view of a sensing node from FIG. 3;

FIG. 10A is a front view of a sensing node from FIG. 3 including a PCB;

FIG. 10B is a top view of a sensing node from FIG. 3 including a PCB;

FIG. 10C is a side view of a sensing node from FIG. 3 including PCB;

FIG. 10D is a perspective view of a sensing node from FIG. 3 including a PCB;

FIG. 18 is a table of which sensor nodes types react to which target gases;

DETAILED DESCRIPTION

Described embodiments generally relate to methods, systems, devices and applications for use in relation to the detection of chemical vapours. Some embodiments relate to systems for the detection of chemical vapours. Some embodiments are directed to portable devices for the detection of chemical vapours and the signalling of an alarm when vapours are detected. Some embodiments are directed to replaceable sensing nodes or modules for use in devices for the detection of chemical vapours. Some embodiments relate to applications for use with devices for the detection of chemical vapours.

Illustrated embodiments shown in FIGS. 1 to 20 relate to a chemical vapour detection device 100, its components, methods of operation, and related software. Device 100 may use colour-change substrates 410 to sense for target chemical vapours at or below pre-set concentrations in an environment local to device 100. The change in colour of substrates 410 due to exposure to a target chemical is detected opto-electronically, allowing an automatic alarm to be triggered to warn a user or a nearby system of the likely presence of a harmful chemical. The response time of device 100 may be less than 10 minutes, and may be less than 1, 2, 3, 4, 5, 6, 7, 8, or 9 minutes in some embodiments.

While some illustrated embodiments show colour-change substrates 410, in some other embodiments of the device 100, substrates 410 may react to contact with a target chemical vapour by a change in a different property of the substrate. For example, substrate 410 may exhibit a change in fluorescence, resistance or capacitance when substrate 410 comes into contact with a target chemical vapour. In some other embodiments, the target chemical vapour may deposit material onto substrate 410 rather than reacting with it. Where material is deposited onto substrate 410, this may be detectable by optical, electrical or other means.

Substrates 410 are contained within a plurality of sensor nodes 200, which may be in the form of manually replaceable or swappable single-use or multi-use chemical vapour sensing units, such as cartridges, capsules, cells, cassettes, pods, modules or components. This gives device 100 the flexibility of sensing for multiple chemical vapours, and for the target vapours for detection to be selectable by choosing sensor nodes 200 having the appropriate substrates 410. Using multiple nodes 200 also allows device 100 to use the cross-reactivity of the substrates with various chemical vapours to more precisely pinpoint a detected chemical vapour.

Figure 1:
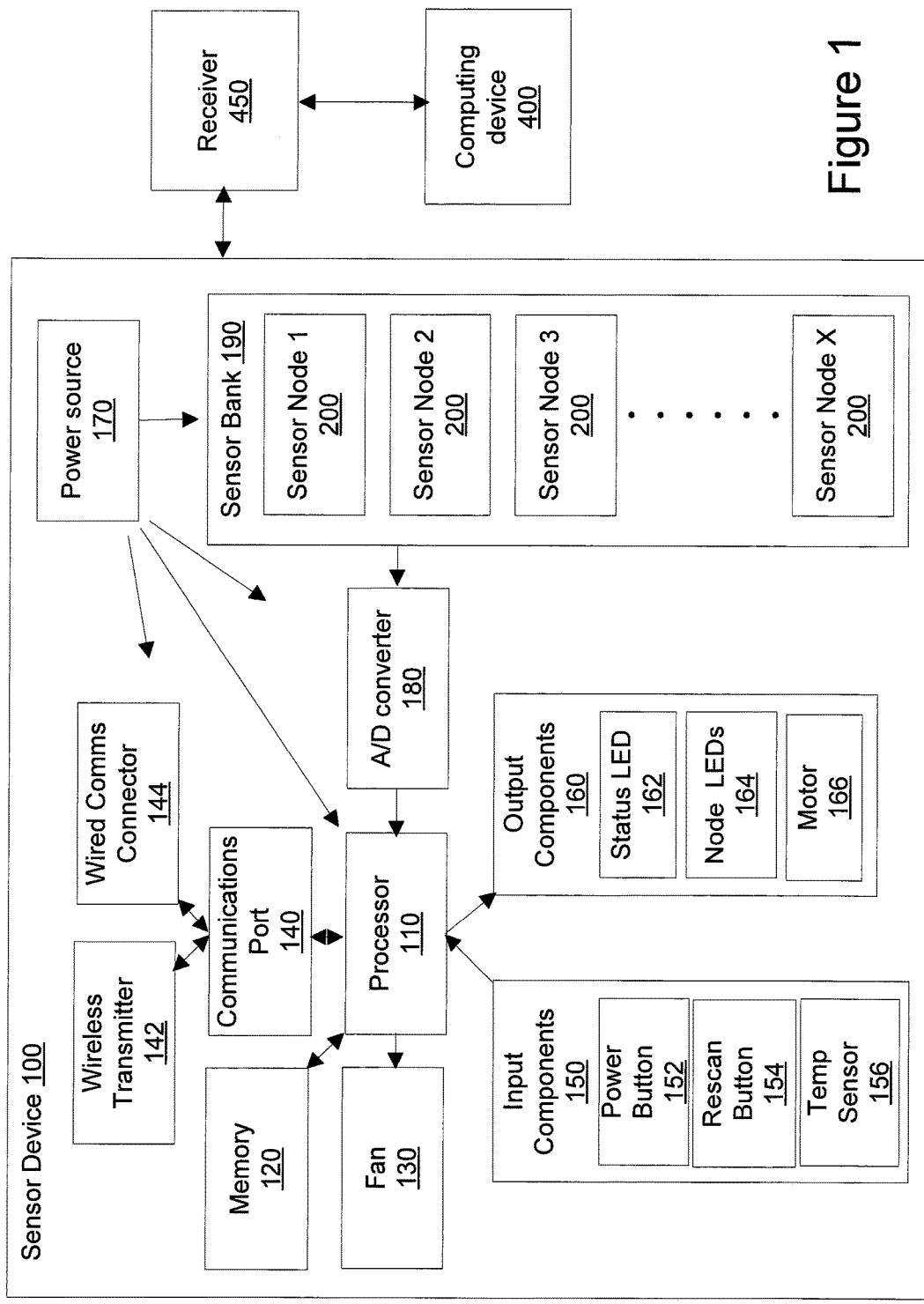
FIG. 1 is a block diagram of a sensing system including a sensing device and sensing nodes according to some embodiments.
Figure 2:
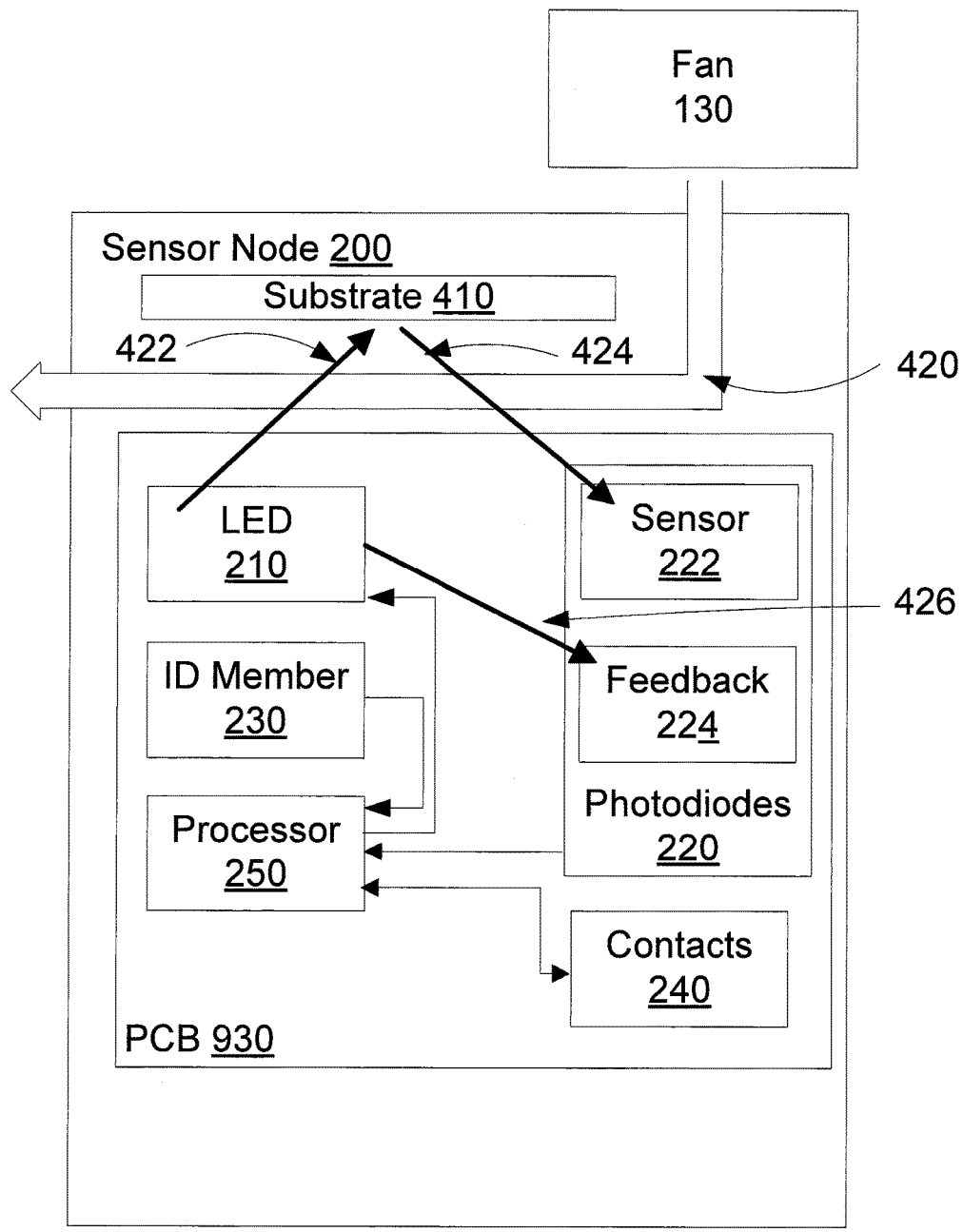
FIG. 2 is a block diagram of a sensing node of FIG. 1.

FIG. 1 shows a sensor device 100 having a bank 190 of sensor nodes 200. Device 100 may weigh less than 500 g, and may weigh less than 100 g, 200 g, 300 g or 400 g in some embodiments. Device 100 has a housing 300, best shown in FIGS. 3 to 6 and 8, and electronic components mounted on a PCB 360, best seen in FIG. 7. Housing 300 may be integrally formed as one component, or be made up of several parts. The electronic components may include a processor 110, memory 120, fan 130, a communication component, such as a communications port 140, input components 150, output components 160, a power source 170, and an analogue to digital (A/D) converter 180. PCB 360 may also house other electronic components, such as general purpose input/output (GPIO) expanders, low drop-out (LDO) linear voltage regulators, header pin interfaces and connectors, for example. Housing 300 may be of a size to be hand-held or manually portable.

Processor 110 may include a microprocessor or a microcontroller such as the Atmel AT91SAM7X256 microcontroller. In some embodiments, processor 110 may include multiple processors, and may also or instead include components such as digital signal processing units (DSPUs), central processing units (CPUs), arithmetic logic units (ALUs) and registers for storing data.

Memory 120 may be accessible by processor 110 to store and retrieve data. Memory 120 may include read-only memory (ROM) such as erasable ROM (EROM) and electrically erasable programmable ROM (EEPROM or flash ROM), or random access memory (RAM) such as static RAM (SRAM), dynamic RAM (DRAM) or non-volatile RAM (NVRAM or flash).

Fan 130 may act as a means or mechanism for controlling airflow through the device 100 and may be controlled by processor 110 in order to direct air towards the sensor nodes 200 in sensor bank 190. Some embodiments may use an alternative mechanism for controlling airflow through the device 100 and forcing air into plenum 350. For example, some embodiments may use a piezoelectric flapper, pump or bellows. Some embodiments may rely on a passive flow of air through the device, for example in applications where the device 100 is likely to be coupled to a moving object.

Fan 130 may be run by a motor assembly and drive circuitry. Fan 130 may be run at less than 100% duty cycle in order to reduce current draw and extend life of power source 170. For example, fan 130 may be run at 90%, 80% or 70% duty cycle, or some other duty cycle in some embodiments. In some embodiments, fan 130 may produce an airflow of less than 20 liters per minute, which may be between 0.1 and 10 liters in some embodiments. In some embodiments, the airflow may be around 1.5 liters per minute. Fan 130 may run at between 5000 rpm and 30,000 rpm in some embodiments, or optionally between 10,000 and 20,000 rpm. In some embodiments, fan 130 may run at around 15,000 rpm.

Communications port 140 may communicate with processor 110 in order to allow device 100 to communicate with external computing devices. Communications port 140 may support wireless communications through a wireless transmitter 142. Wireless communication may be performed using Bluetooth or Wi-Fi, or another wireless protocol. Wireless transmitter 142 may be calibrated to transmit with a 2.4 GHz wireless frequency, at a data rate of 1 Mbs in some embodiments. In alternative embodiments, a different wireless frequency and data rate may be used, that is adapted to be received by a selected wireless receiver. A wireless transmission mode may be chosen that reduces on-air transmission time to save power. For example, the transmission mode may cause transmitter 142 to be in a low-power or sleep mode in between transmitting and receiving. In some embodiments, wireless transmitter 142 may include the Nordic VLSI nRF240x transmitter, and ShockBurst transmission mode may be used. In order to avoid on-air collision, wireless transmitter 142 may send multiple transmissions with a random delay between packets.

Communications port may also or alternatively support wired communications through a wired communications connector 144, which may be a socket to receive a cable such an a universal serial bus (USB) cable, Ethernet cable, or other cable for wired communications. Wired communications may use the USB protocol in some embodiments, or another suitable wired communications protocol. Device 100 may have a USB or microUSB port to allow for data transfer using USB in some embodiments.

Some embodiments of device 100 may further include (or be coupled or coupleable to) a global positioning system (GPS), accelerometers, gyroscopes or sensors, such as skin temperature sensors, core body temperature sensors, blood oxygen saturation sensors, metabolic indicator sensors, heart rate or pulse sensors. These sensors may allow a user's location, health and vital signs to be monitored while they are using device 100. An environmental sensor such as temperature and/or humidity sensor 156 may also be used to monitor the user's environment.

Processor 110 may receive data from input components 150 as well as sensor bank 190. Input components 150 may include buttons such as power button 152, rescan button 154 and temperature and/or humidity sensor 156. Input components 150 may activate electrical signals which are communicated to and interpreted by processor 110. For example, pressing buttons 152 or 154 may activate signals that communicate that the respective button has been pressed. Pressing power button 152 may cause processor 110 to power device 100 on or off Pressing on rescan button 154 may cause processor 110 to communicate with sensor bank 190 to scan for sensor nodes 200 that have been plugged into the device. In some embodiments, pressing rescan button 154 may also cause processor 110 to reset device 100 when an alarm has gone off, in order to allow further sensing to take place. Buttons 152 and 154 may be push button switches such as the TE Connectivity c-1-1437565-8-d1-3d push button switches.

Temperature and/or humidity sensor 156 may produce electrical signals corresponding to a measured temperature or humidity, and processor 110 may be able to interpret these signals in order to determine what temperature and/or humidity device 100 is operating in. This information may be used to allow device 100 to calibrate correctly for various environmental conditions, by electronically filtering data that may be affected by changes in temperature or humidity. In some embodiments, sensor 156 may be a digital humidity and temperature sensor such as the Sensirion SHT2x.

Processor 110 may also control output components 160. Output components 160 may include a status light emitting diode (LED) 162, sensor node LEDs 164 and motor 166. Bi-colour LEDs, such as the Avago Technologies HSMF-C16X LEDs may be used in some embodiments. Processor 110 may control the power supplied to LEDs 162 and 164 to cause them to flash, or to glow in different colours to indicate different statuses of device 100. For example, processor 110 may cause status LED 162 to emit a green light to indicate that device 100 is charged, red light to indicate low power and that device 100 needs charging, and a flashing red light to indicate that device 100 is charging. In some cases, LED 162 may be an infra-red LED, so that the device can be used in situations without attracting attention. Processor 110 may cause sensor node LEDs 164 to flash or glow a particular colour to indicate whether a node 200 has been properly identified, or if node 200 has detected a chemical vapour, for example. Processor 110 may also control motor 166 to generate a tactile alarm to alert the user by way of vibration, in case they cannot see LEDs 162 and 164. Motor 166 may be responsive to an activation control signal generated by processor 110, which may cause device 100 to vibrate to indicate the alarm has gone off. In some embodiments, device 100 may have further visual and non-visual output components 160. For example, device 100 may have an LCD panel, screen, speaker, or buzzer to provide output to the user. In some embodiments, device 100 may be in wireless or wired communication with a headset, heads-up display or headphones set to which an output may be transmitted for visual or non-visual communication to the user.

The electronic components of device 100 may be powered by a power source 170. Power source 170 may supply power to sensor bank 190, processor 110, output components 160 and fan 130, as well as other electronic components of device 100. Power source 170 may be a battery or a rechargeable battery pack, such as a lithium ion pack. For example, a lithium ion (LiOn) polymer 3.7V rechargeable battery might be used in some embodiments. A larger pack may be required if a longer battery life is desired. Sensor device 100 may include charging circuitry and for charging power source 170, which may include a socket for plugging device 100 it into a mains power point. Some embodiments may be rechargeable by USB, having a USB or microUSB connector allowing for the device to be plugged into a USB port for charging. For example, some embodiments may use a Molex microUSB connector 473460001. In some embodiments, power source 170 may communicate its charge level status with processor 110. This allows processor 110 to automatically shut down device 100 when the power is running low, to protect power source 170. In some embodiments, power source 170 may supply power scavenged from the environment, such as through solar panels, or may source power from another device to which device 100 is electrically coupled.

Device 100 may have at least one A/D converter 180 to receive analogue input from sensor bank 190 and communicate the input to processor 110 in digital form. A/D converter 180 may be a 12-bit A/D converter oversampled to 16 bits to give an accuracy of 16 bits.

Sensor bank 190 may hold a plurality of sensing nodes 200 in node receptors 330 defined by housing 300. Receptors 330 may alternatively be described as recesses, receptacles, holders, or receiving portions. Each receptor 330 is specifically sized and shaped to receive one of the nodes 200. Each node 200 may have a total weight of between 5 g and 50 g. The total weight may be in the vicinity of 20 g in some embodiments. For example, in the embodiment shown in FIGS. 3 to 8, sensor bank 190 has eight sensor nodes 200. Each sensor node may be calibrated to detect a different chemical vapour. For example, in some embodiments, respective nodes 200 may be calibrated to detect for ammonia ($NH_3$), chlorine ($CL_2$), hydrogen sulphide ($H_2S$), sulphur dioxide ($SO_2$), hydrogen cyanide (HCN), nitrogen dioxide ($NO_2$), phosphine ($PH_3$) and hydrogen chloride (HCl). In other embodiments, alternative or additional chemical vapours may be detectable by nodes 200. In some embodiments, the vapours may be chemical vapours from biological sources, such as fermentation headspaces, or the combustion or decomposition of organic matter. In some embodiments, these may be toxic industrial chemicals, chemical warfare agents, volatile organic compounds, or chemical vapours harmful to human health. For example, chemicals such as ethylene oxide, hydrogen peroxide, sulphuric acid, nitric acid, nicotine, nitric oxide, chloropicrin, chlorine dioxide, acrolein, strychnine, chemical warfare agent (CWA) sulphur mustard (HD), CWA sarin (GB), CWA VX (O-ethyl S-[2-(diisopropylamino)ethyl]methylphosphonothioate), methyl isocyanate, methyl bromide, CWA phosgene, CWA lewisite, methyl thiosocynate, and sulfuric difluoride may be detected by some nodes 200. Each sensor node 200 may be labelled on an upper surface (that is visible when the node 200 is seated in the receptor portion 330) with the chemical vapour which it is targeted towards. The label allows the user to identify the chemicals being sensed by the nodes 200, and associate any signals displayed by LEDs 164 to the relevant chemical vapour.

In some embodiments, device 100 may communicate with an external computing device 400. Computing device 400 may be a personal computer (PC), laptop, personal digital assistant (PDA), smart phone, tablet computer or other computing device capable of receiving data from sensor device 100 via a wireless receiver 450. The computing device 400 may record data received from device 100 in on-board memory for processing and/or later review by the user. Device 100 may also communicate with other devices 100. For example, a series of devices 100 may be situated locally to one another and may communicate to allow for the detection of more vapours than a single device 100 can cater for. For example, where each device 100 can hold eight vapour sensor nodes 200, two devices 100 may be used to allow for sixteen nodes 200 to be used at once.

Receiver 450 may have a USB or microUSB connector to allow for data transfer via a USB port with computing device 400. Data sent by device 100 through wireless transmitter 142 may be data retrieved from data storage, such as from memory 120, for post-operations analysis, or data may be wirelessly communicated in real time as the data is received from sensor bank 190. Receiver 450 may be able to receive data from device 100 up to a range of 200 m with line-of-sight. Receiver module 450 may have a 2.4 GHz wireless frequency and a 1 Mbs wireless data rate, and may have a USB 2.0 PC interface to communicate with a PC such as computing device 400. Receiver 450 may be chosen to be compatible with wireless transmitter 142, and selection may also be based on the protocol on which receiver 450 operates. For example, in some embodiments, receiver 450 may operate on a protocol which uses a short packet which is sent without acknowledgement. This protocol would minimise on-air transmission time and minimise collisions with packets from other devices. This would also reduce battery use by the receiver 450.

Other components on PCB 360 may include a GPIO expander such as the Exar Corporation XRA1201P, which may help to control the input and output signals of the device to free up processor 100 for other functions. They may also include a LDO linear voltage regulator such as the Rohm Semiconductor BD15IA5WEFJ-E2 to assist in maintaining a steady voltage. Further components may include header pin interfaces, such as the Samtec SIR1-05-X-S, and connectors such as the Hirose Electric DF12E(3.0)-20DP-0.5V, the Molex 0734120110, and the Omron Electronics XF2L-1025-1A, for example. PCB 360 may be coated with a protective coating to protect it from environmental factors such as moisture and dust, and to reduce the likelihood of damage to the components.

Sensor bank 190 may contain a number of sensor nodes 200. Sensor nodes 200 may have a housing 900 and electronic components contained on a PCB 930. A diagram of the functional components of each of sensor nodes 200 is shown in further detail in FIG. 2. The electronic components of sensor node 200 may include a light emitting component, which may include a wavelength tuneable light source such as LED 210, optically sensitive components such as photodiodes 220, an identification component or identification circuitry such as ID member 230, a processor 250, and a signal coupling portion, such as contacts 240, through which sensor node 200 is in communication with device 100. In the illustrated embodiment, node 200 is electrically connected to device 100, but in some other embodiments the signal coupling portion may include other signal coupling components, such as optical communication components. Sensor node 200 may further include a chemically sensitive substrate 410.

LED 210 may be directed to emit light 422 onto substrate 410. Light 424 may be reflected off substrate 410 and detected by a sensing element, which may be a photosensitive element, such as sensor photodiode 222. Substrate 410 may be a one-use replaceable substrate, which changes colour in the presence of a particular target chemical vapour. LED 210 may be driven by a pulsed constant current from power source 170, controlled by processor 250. In some embodiments, the light may be reflected off of two identical substrates in series (see FIGS. 9 to 12, 15A and 15B), or it may be reflected twice off of a single curved substrate 410. These substrates may be positioned to create a specific light path length between LED 210 and sensor 222, which may be determined as an optimal length to allow for accurate sensing. LED 210 may emit light of wavelengths inside or outside the visible spectrum, and may be a broad spectrum light source in some embodiments.

Figure 20:
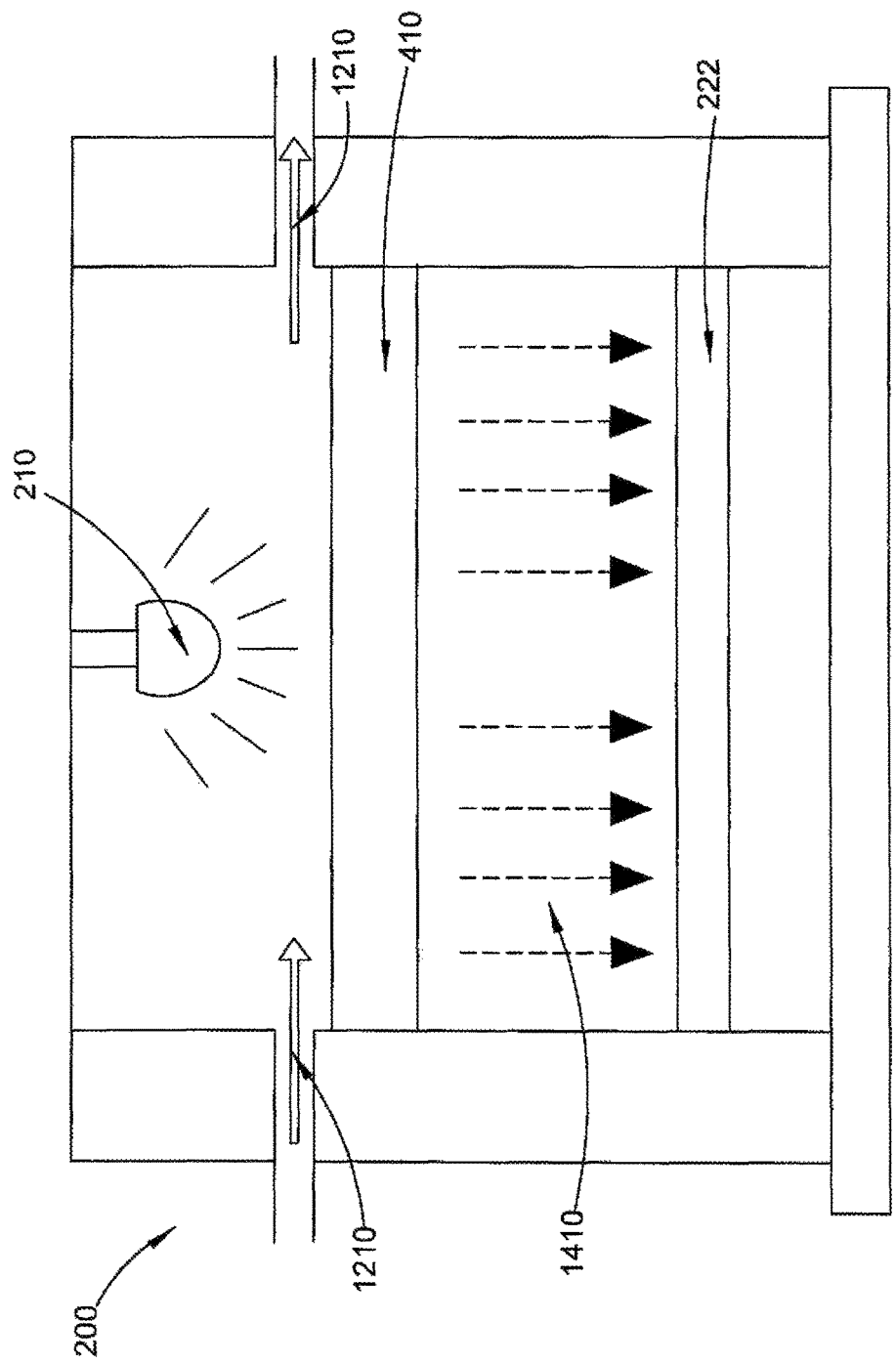
FIG. 20 is a block diagram of an alternative sensing node of FIG. 1.

In another embodiment, shown in FIG. 20, node 200 may have a substrate 410 positioned between a light source 210 and sensor photodiode 222. In such embodiments, light 1410 travels through substrate 410 before reaching photodiode 222, so that the light received by photodiode 222 would depend on the light (colour) transmission properties of substrate 410. A change in opaqueness or colour of substrate 410 can be detected by photodiode 222.

A calibration element such as feedback photodiode 224 may allow for adjustment of LED 210. This may accommodate for the changes in brightness of LED 210 based on factors such as the ambient temperature, for example. Feedback photodiode 224 may measure the LED 210 output directly by receiving a small amount of light directed from LED 210 towards it. This light may be directed through a hole in PCB 930, by optical fibre, or other means. Feedback diode 224 provides a signal to processor 250 based on the intensity of light received. Processor 250 may use the received signal to adjust the current supplied by power source 170 to LED 210 to ensure consistent light output even in changing environmental conditions. For example, changes in LED output due to temperature changes can be accounted for. Photodiodes 222 and 224 may be Advanced Photonix PDB-C154SM PIN silicon photodiodes, and may be blue enhanced. As photodiodes 222 and 224 may be more sensitive at longer wavelengths (i.e. in the red spectrum), a blue enhanced LED may increase sensitivity in the visible and shorter wavelength regions.

Figure 21:
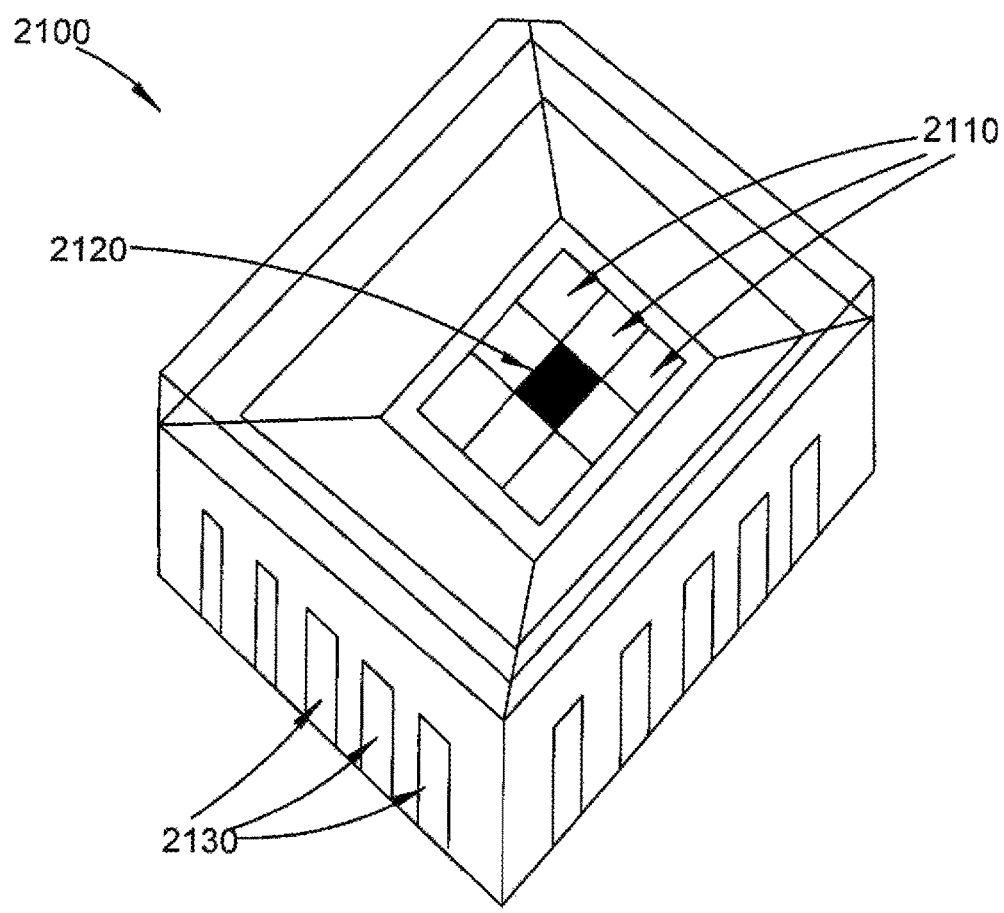
FIG. 21 is a perspective view of a sensing array for use with a sensing node.
Figure 22:
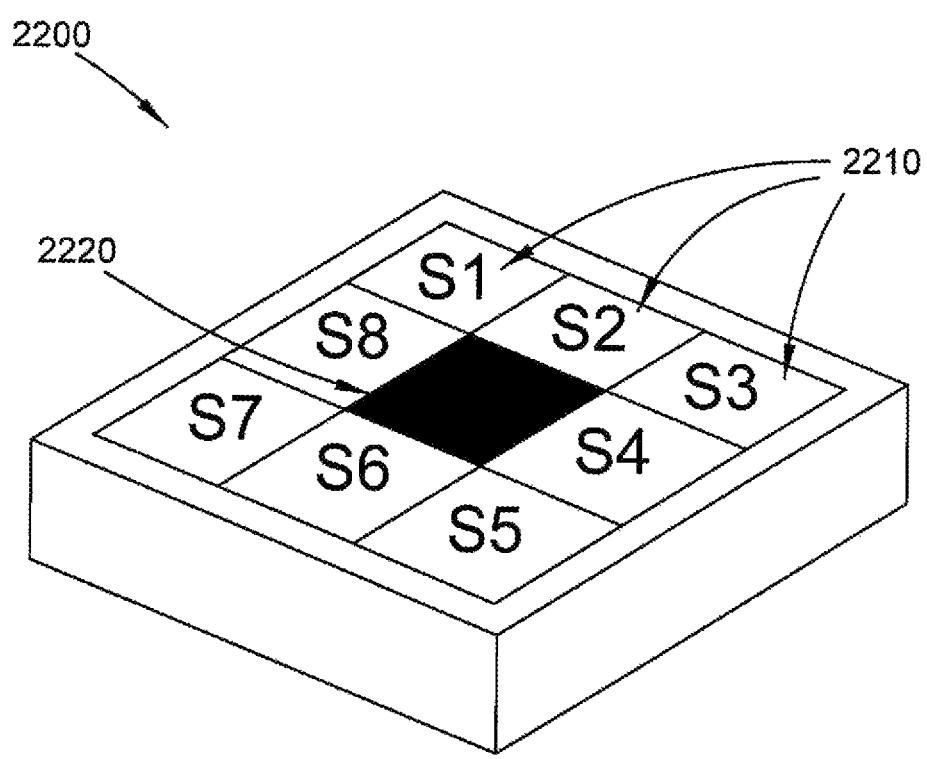
FIG. 22 is a perspective view of a substrate array for use with a sensing node.

In some other embodiments of sensing node 200, an array of sensing sub-elements may be used, such as sensing array 2100 as shown in FIG. 21. Sensing array 2100 may have a number of individual sensing members 2110 connected electronically to contacts 2130. In some embodiments, there may be nine sensing members 2110, for example, which may be arranged as a 3×3 grid. Some sensing members 2110 may be inactive, such as middle sensing member 2120, to allow for easier mounting of sensing array 2100 and easier access to the active contacts 2130. In some embodiments, sensing array 2100 may include a multispectral photodiode, such as the PixelTeq miniaturised 8 band light to voltage converter. It may be component 102387277 from PixelTeq, for example.

An array of substrate sections, such as substrate array 2200 may be used with sensing array 2100 to allow for multiple vapours to be detected while reducing the size of each node 200. Substrate array 2200 may have a grid of substrate members 2210 corresponding to the grid of sensing members 2110 of sensing array 2100. For example, substrate array 2200 may have a 3×3 grid of substrate members 2210. Substrate array 2200 may have inactive areas 2220 corresponding to the location of inactive sensing members 2120 of sensing array 2100. Each sensing member 2100 may be configured to detect for the change in property exhibited by its corresponding substrate member 2210.

In embodiments where sensing array 2100 is used, sensing array 2100 may be positioned below substrate 410 or substrate array 2200, with LED 210 positioned above substrate 410 or substrate array 2200, as shown in FIG. 20, to detect changes in the opacity or transmissivity of substrate 410 or substrate array 2200, for example with respect to certain light wavelengths.

Figure 23A:
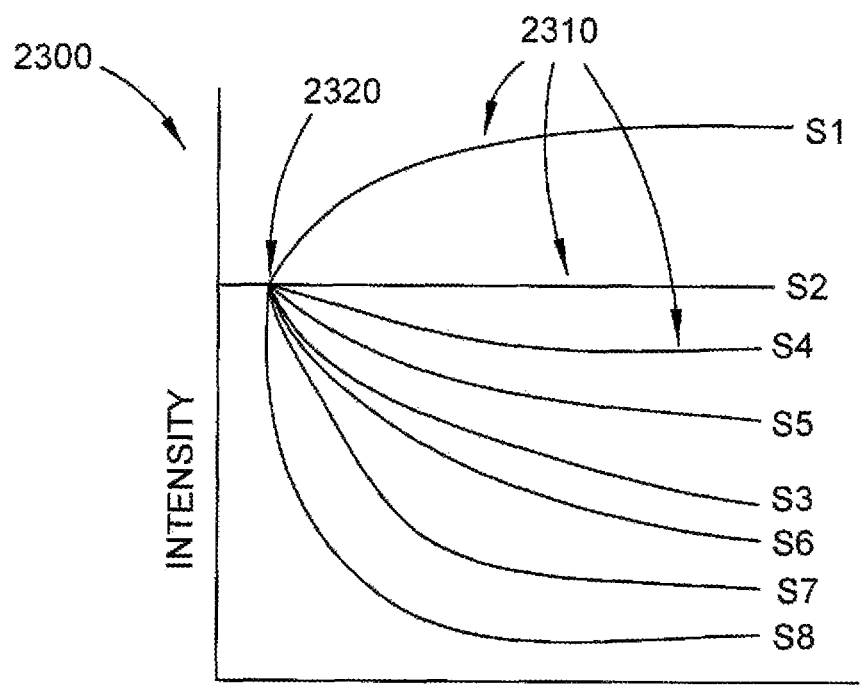
FIG. 23A is a graph showing the intensity response of multiple substrates used with a sensing array.

FIG. 23A shows an example output graph 2300 from sensing array 2100 positioned as per FIG. 20. Each output 2310 corresponds to an individual sensing member 2110, and shows the light intensity detected by the sensing member 2110 over time. The curves indicated by S1 to S8 are not based on actual data, but are provided for purposes of illustration only. In the illustrated example shown in FIG. 23A, the intensity of the signal corresponding to substrate S1 has increased after point 2320, while the intensity of the signals corresponding to substrates S3 to S8 have decreased to varying degrees. The intensity of the signal corresponding to substrate S2 has not changed. This may indicate that substrates S1 to S8 came into contact with a chemical vapour at a time corresponding to point 2320. Substrate S1 may have undergone a reaction that caused it to become more transparent, so that a larger transmission of light occurred and the intensity of the output 2310 of the corresponding sensing member 2110 increased. Substrates S3 to S8 may have undergone a reaction to become more opaque, with S8 becoming the most opaque. The reaction may have reduced the amount of light transmitted by these substrates, and decreased the output 2310 of the corresponding sensing members 2110. Substrate S2 may not be sensitive to the chemical vapour, and may not have changed in opacity, so that the output 2310 of the corresponding sensing member 2110 has remained constant.

In an alternative embodiment, sensing array 2100 may be used with a single substrate 410. Each sensing member 2110 may be configured to detect for a different wavelength. This arrangement may be used with a single light source, which may be a broad spectrum light source, or with multiple light sources. In some embodiments, the light sources may include multiple LEDs 210, each having a different wavelength, and each flashing alternatively. This may allow for a fingerprint of the spectrum of the light received from substrate 410 to be constructed by processor 110, allowing more accurate identification of the chemical vapour detected.

Figure 23B:
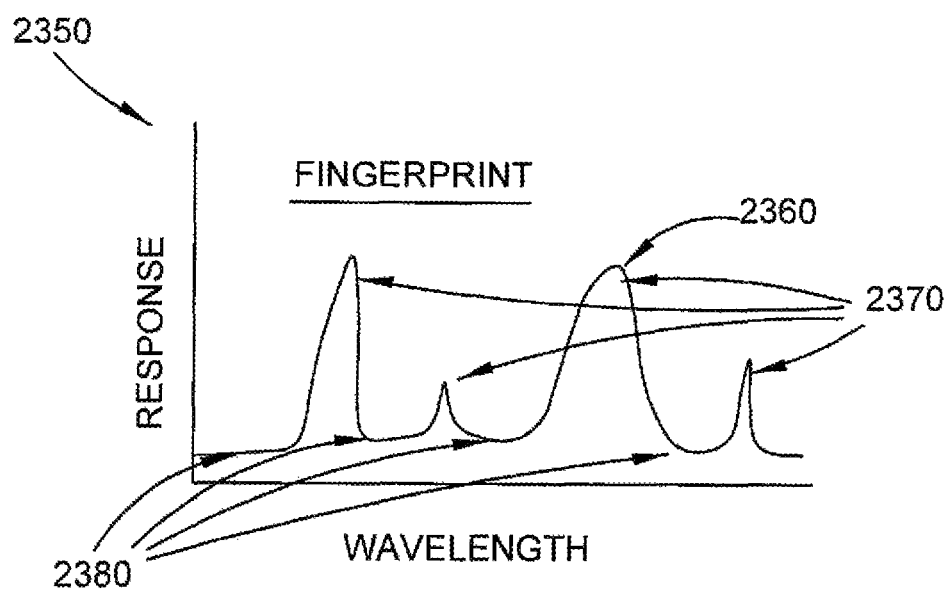
FIG. 23B is a graph showing the intensity response of multiple wavelengths of a single substrate used with a sensing array.

An example graph 2350 of the fingerprint 2360 showing the response of different wavelengths of light based on this arrangement is shown in FIG. 23B. The curve indicated by 2360 is not based on actual data, but is provided for purposes of illustration only. The spikes 2370 correspond to wavelength values with a strong response. These wavelengths may have been strongly transmitted by substrate 410. Valleys 2280 correspond to wavelengths that were not strongly transmitted by substrate 410. Graph 2350 may be compared to a graph of a known wavelength response of the substrate 410 before it has come into contact with a chemical vapour. Comparing the graphs may show whether the response to any of the wavelengths has changed, which may indicate that substrate 410 has reacted to a chemical vapour. Comparing the overall graph 2350 to known response values of substrate 410 may allow the chemical vapour that substrate 410 came into contact with to be identified. The optical parts of each sensor node 200, such as LED 210 and photodiodes 220, may be coated with a surface treatment, which may be a hydrophobic, hydrophilic, superhydrophobic or superhydrophilic treatment, to prevent fogging in high humidity environments. Using a hydrophilic surface treatment may attract a layer of condensate to the optical elements that would create an even layer of liquid on the surface of the component and prevent droplets of moisture from forming that may affect the operation of the optical components. Droplets of water or fogging of the components may cause light passing through them to be dispersed, causing a drop in the intensity of the light received by photodiode 222. A hydrophilic surface coating may reduce the change in intensity, or may cause a slight increase in intensity of the light received. Hydrophilic surface treatments may include oxygen plasma, polymers applied by plasma or mixtures of surfactants or detergents, either alone or in combination. In some other embodiments, different means may be used to deal with humidity or moisture in the nodes 200. For example, water may be evaporated by a heat source, or driven out by a fan or pump.

Each sensor node 200 may have substrates 410, LED 210 and photodiodes 220 tuned to detect a different chemical vapour. The substrate 410 of each chemical may be selected to change colour when it comes into contact with one or more chemical vapours. The wavelength of light from LED 210 may be selected or tuneable to a wavelength that will best highlight the reflectance change of the substrate, so that sensor photodiode 222 can most easily sense the change in intensity of the reflection when a chemical vapour interacts with substrate 410. Alternatively, LED 210 may be a broad spectrum light source, and sensor photodiode 222 may be tuned to detect intensity changes in a specific wavelength or small band of wavelengths. This might be a wavelength of light inside the visible spectrum or the outside the visible spectrum. In some embodiments, node 200 may have multiple LEDs 210, with each LED tuned to a different wavelength. This may allow for the sensing of different colour changes in a single substrate. LEDs 210 may be configured to flash alternatively, to avoid interference between light sources. In some embodiments, LEDs 210 may be LEDs operating at a wavelength outside of the visible spectrum, for example in the infra-red (IR) or ultra-violet (UV) spectrum. Photodiode 222 may sense for either an increase or decrease in the measured intensity. Sensor photodiode 222 may also be tuned to detect the specific colour change predicted to occur. In some cases, ultra-violet (UV) or infrared (IR) intensity changes may be detectable, using UV and IR LEDs and photodiodes. In some embodiments, LED 210 and photodiode 222 may be tuned to detect a change in the wavelength reflected by substrate 410. LED 210 may be controlled by signals from processor 250 to operate at less than 100% duty cycle, such as at a duty cycle of 90%, 80%, 70%, 60%, 50%, 40%, 30% 20% or 10%, or between 1% and 10%, for example. For example, LED 210 may be controlled to flash at a frequency of 1 Hz, to avoid bleaching substrates that may be chemically sensitive to high intensity light sources.

Substrate 410 may comprise a material at least one property of which is caused to change when the material comes into contact with a target vapour. In some embodiments, the property may be a colour, conductivity, fluorescence, capacitance or inductiveness of the material. In some embodiments, substrate 410 may comprise a structural layer, which may include a filter paper, such as Whatman #1, or other high surface area material, for example a thin layer chromatography (TLC) plate, saturated with a solution including a dopant, a property of which changes when the dopant comes into contact with a target chemical vapour. In some embodiments, the dopant may produce a colour change when in contact with a target chemical vapour. In some embodiments, the dopant may be painted on to the filter paper. The dopant concentration and substrate selected may be dependent on the chemical vapour being targeted. A list of optimum conditions for a selection of substrate types is displayed below in Table 1.

TABLE 1

Example substrate parameters for selected target chemical vapours

| Target chemical vapour | Reactive method | Colour change |
|---|---|---|
| Ammonia | 0.3125% (w/v) Bromophenol blue in Dimethylacetamide (DMAc) doped on 50% silanised glass backed silica TLC plate. Dried on hotplate at 100° C. Exposed to HCl vapour until persistent yellow/orange appearance | Yellow/orange to blue |
| Chlorine | Ethanolic/glycerol solution (4:1) of o-tolidine (10 mg/mL) + orthophosphoric acid (1 mg/mL) doped on Whatman #1 paper and dried in airflow for 1 hour | Beige to blue/green |
| Hydrogen sulphide | Saturated aqueous solution of lead (II) acetate doped on Whatman #1 paper and allowed to dry in airflow for 1 hour | White to yellow/brown |
| Sulpher dioxide | Aqueous solution of sodium nitroprusside (4% w/v) and sodium carbonate (2% w/v) doped onto Whatman #1 and allowed to dry in airflow for 1 hour | Amber/yellow to orange/red |
| Hydrogen cyanide | Whatman #1 is doped with aqueous solution of Congo Red (0.05% w/v) and dried immediately using hot airflow. Doped substrate is then exposed to an aqueous solution of silver nitrate (5% w/v) and then dried immediately under hot airflow. | Purple to blue |
| Nitrogen oxide | Methanolic solution of 10 mg/ml diphenylamine (10 mg/mL) and oxalic acid (12.5 mg/mL) is doped onto normal phase foil backed silica TLC plate. Substrate allowed to dry for 1 hour in airflow | White/beige to yellow/brown |
| Phosphine | 0.1N silver nitrate in DMAc is doped onto foil backed silica and substrate allowed to dry for 3 hours in airflow | White/beige to brown/red |
| Hydrochloric acid | Chloroform solution of NFA32D (1 mg/mL) doped on Whatman #1 paper. Substrate ready to use upon evaporation of chloroform | Pale yellow to yellow (observed fluorescence change under longwave UV) |

After saturation with, or other application of, the dopant, the filter paper may be dried and cut to size to produce substrate 410. In some embodiments, substrates 410 may be around 6 mm×6 mm in size. Substrates may be placed into sensor nodes 200 shortly after being prepared, as they may be air and light sensitive. Sensor nodes 200 and substrates 410 are preferably stored in a dark and inert gas atmosphere, optionally with controlled humidity. In some embodiments, substrate 410 may be coated with a humectant such as glycerol after saturation with the dopant.

Substrate 410 may need to be backed by a rigid or semi-rigid backing material in some cases, if substrate 410 is too thin, to provide rigidity and keep substrate 410 flat. The backing material may be a glass slide, for example. In some other embodiments, substrate 410 may be curved or bent. In some embodiments, substrates 410 may include a dopant suspended in an ink, dye or paint applied to a backing material. The dopant may be contained within the plastic or other material making up the body of node 200.

ID member 230 allows for the identification of the node by device 100. Sensor nodes 200 with different substrate materials 410 may be fitted with different ID members 230, so that they can be easily identified by device 100. The ID member 230 may be used by processor 110 of device 100 as a unique identifier to identify which chemical vapour or vapours sensor node 200 can detect. In some embodiments, ID member 230 may be an electronic component having a predetermined value, such as a resistor with a unique value. In other embodiments, ID member 230 may be an ID number or code stored on memory accessible by processor 250. In some embodiments, ID member may be a barcode, quick response (QR) code, radio frequency identification (RFID) chip, or other means of identification that can be read or interpreted by processor 250 or otherwise communicated to processor 110.

Housing 900 of sensor node 200 provides an airflow path 420 from fan 130 past substrate 410. This allows substrate 410 to come into contact with any chemical vapour in the air that substrate 410 may be configured to detect. If such a chemical vapour is present, substrate 410 is caused to change colour by way of a chemical reaction between the dopant in the substrate material and the chemical vapour. As a result of the chemical reaction, reflected light 424 from LED 210 may change in intensity, or may be re-emitted at a different wavelength, and the change is detected by sensor photodiode 222. A change in reflectance due to chemical vapour interaction with substrate 410 is translated to a change in voltage supplied by sensor 222, which is detected by processor 250. Processor 250 then communicates this change to processor 110. Processor 110 monitors the data signals received from node 200. If processor 110 detects that the data signals received from node 200 reach a predetermined threshold value, processor 110 may determine that an alarm condition has been met, and may cause an appropriate alarm to be set off. The predetermined threshold value may be reached when the voltage from sensor 222 passes one or more pre-set limits for that sensor node 200 that indicates a target chemical vapour has been detected.

Processor 250, may include a microprocessor or a microcontroller such as the Atmel AT91SAM7X256 microcontroller. In some embodiments, processor 250 may include multiple processors, and may also or instead include components such as digital signal processing units (DSPUs), central processing units (CPUs), arithmetic logic units (ALUs) and registers for storing data. Processor 250 communicates with LED 210, photodiodes 220, and ID member 230 on sensor node 200, as well as communicating with processor 110 through contacts 240.

Contacts 240 allow for communication between sensor nodes 200 and device 100. Contacts 240 may be arranged to be in electrical communication with a set of contacts 335 on device 100 when sensor node 200 is positioned on device 100. Contacts 240 may facilitate communication through electrical, optical, or other means. In some embodiments, contacts 240 are conductive contacts that may be made of silver, gold, platinum, palladium, or another electrically conductive metal, alloy or polymer.

Figure 3:
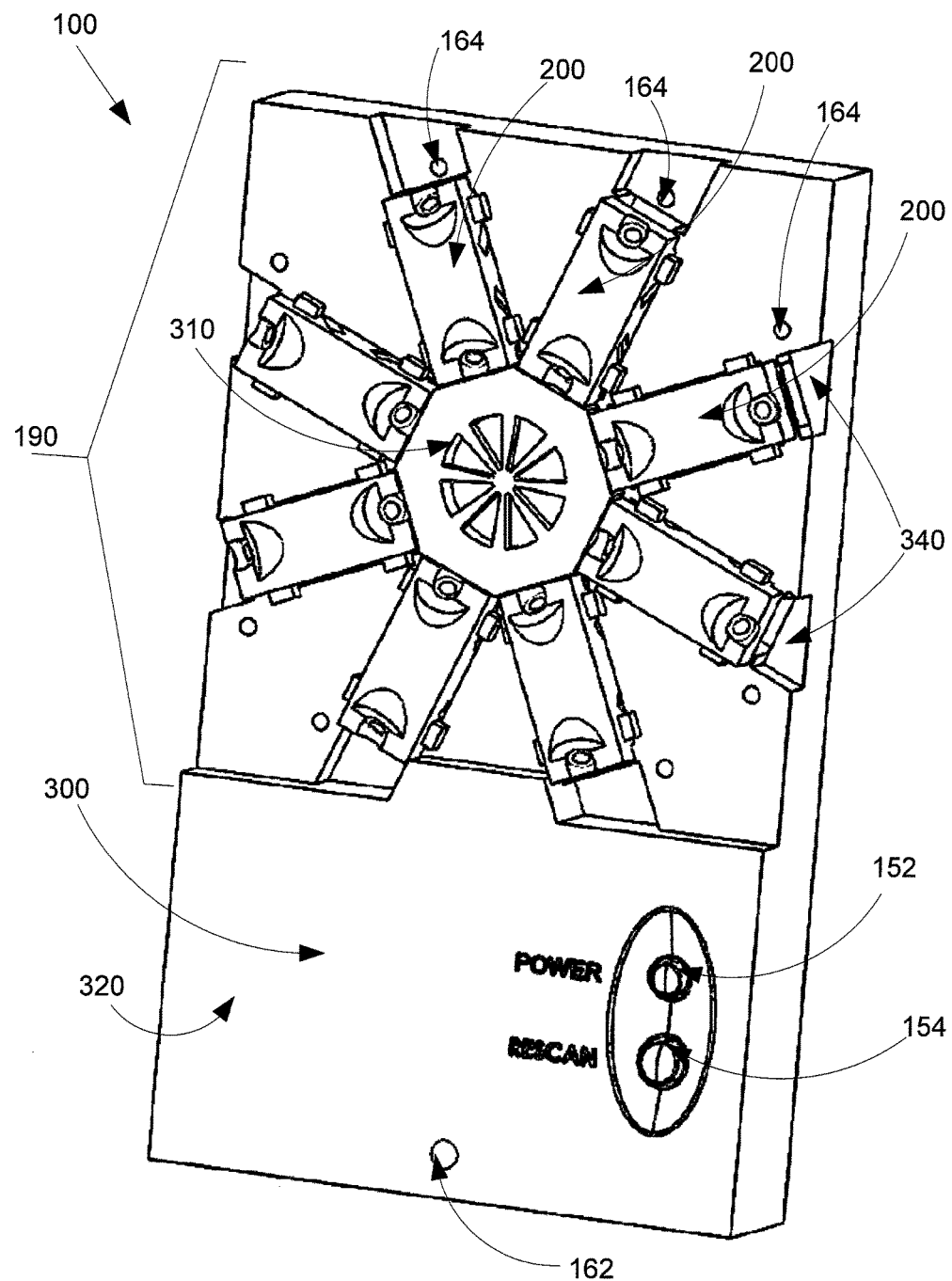
FIG. 3 is a top perspective view of a chemical vapour sensing device according to some embodiments.
Figure 4:
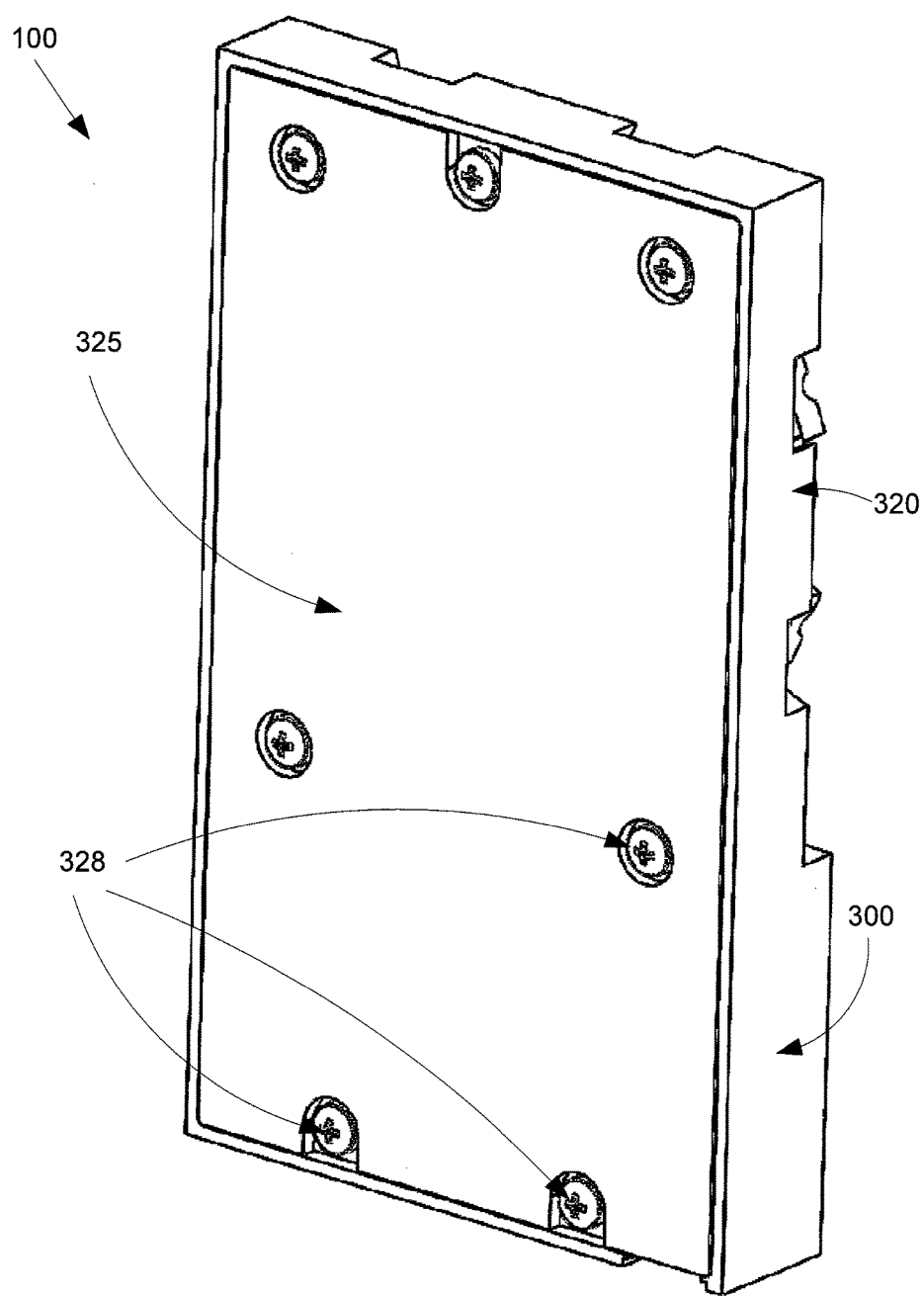
FIG. 4 is a bottom perspective view of the device of FIG. 3.

FIG. 3 shows a perspective view of an embodiment of sensing device 100. Sensor device 100 has housing 300. Housing 300 may comprise a front cover 320 and back cover 325 (see FIG. 4) which may each be integrally formed of a moulded polymer or other suitable material. Housing 300 may further comprise side walls and end walls, which may be part of front cover 320 in some embodiments. In some embodiments, housing 300 may be made as a single piece, or may be made up of multiple housing parts. Housing 300 may be approximately rectangular in shape, and may be sized to be handheld, roughly the size of a smart-phone or small tablet computing device. Housing 300 encases an electronics package which may be carried on a printed circuit board (PCB) 360 (shown in detail in FIG. 7). Housing 300 may allow user access to inputs and output components 1150 and 160 of the device. For example, housing 300 may provide access to buttons 152 and 154, and allow the user to see LEDs 162 and 164. Front cover 320 may have a fan cover 310 in a central position of device 100 which contains fan 130 mounted on fan mount points 355 within a fan recess or plenum 350 (best seen in FIGS. 6 and 12).Fan cover 310 may have a plurality of apertures to allow air to pass through cover 310 to fan 130. Fan 130 is driven by an internal motor (not shown) which is connected to driver electronics by wired contacts (not shown).

In some embodiments, housing 300 may further comprise a cover 1450 (shown in FIG. 14B) to sit over sensor bank 190. The cover may be hinged or clipped to allow access to the nodes 200 when the cover is open and may have transparent or semi-transparent sections to permit light from the LEDs 162, 164 to be visible through the cover. The cover may be formed of a plastic material or one or more other suitable materials. The cover may be fully formed or partly formed of a similar material to the material of the body of the housing 300. The cover may cooperate with the contours and/or shape of the housing 300 to define inlet and outlet airflow paths for allowing vapours in the local environment to reach the sensor nodes 200.

Fan 130 and housing 300 are configured to equally distribute air to each of the sensor nodes 200 in sensor bank 190. Sensor nodes 200 may be arranged in an array around fan 130, and may be positioned in a radial distribution around and equidistant from plenum 350 and fan 130. Such an arrangement allows fan 130 to take in air from immediately in front of device 100 and to supply air of equal pressure and flow rate to each sensor node 200, while minimising the distance the air has to travel between fan 130 and each substrate 410. Furthermore, an independent one-directional air supply is provided to each node 200, meaning that the air doesn't travel between sensor nodes 200, which prevents contamination of the air by any chemicals within each sensor node 200. In some embodiments, device 100 may have airflow apertures and corresponding fans (or other airflow control means) on the back, side, or on another location of the device, instead of or in addition to the plenum 350 and fan 130 as described. These additional or alternative airflow apertures may allow air to flow from the back or side of device 100 and through sensor nodes 200. In some embodiments, fan 130 may be configured to draw air from a single inlet, such as through plenum 350, and distribute it along multiple flow paths to multiple outlets, such as through nodes 200. In some embodiments, the airflow path may be reversed, and one or more fans 130 (or other airflow control means) may be configured to pull air from multiple inlets along multiple flow paths (i.e. through nodes 200) and out of one air outlet, such as plenum 350.

While illustrated embodiments show eight sensor nodes 200 surrounding a centrally placed fan 130 in a radial arrangement, other arrangements are envisioned. For example, more or fewer sensor nodes 200 may be used. Alternatively, sensor nodes may be placed in rows or columns, or in a grid-like arrangement in some embodiments. Furthermore, device 100 may have multiple fans 130 supplying air to one or more groups of the sensor nodes 200, in multiple radial or other arrangements.

Figure 14A:
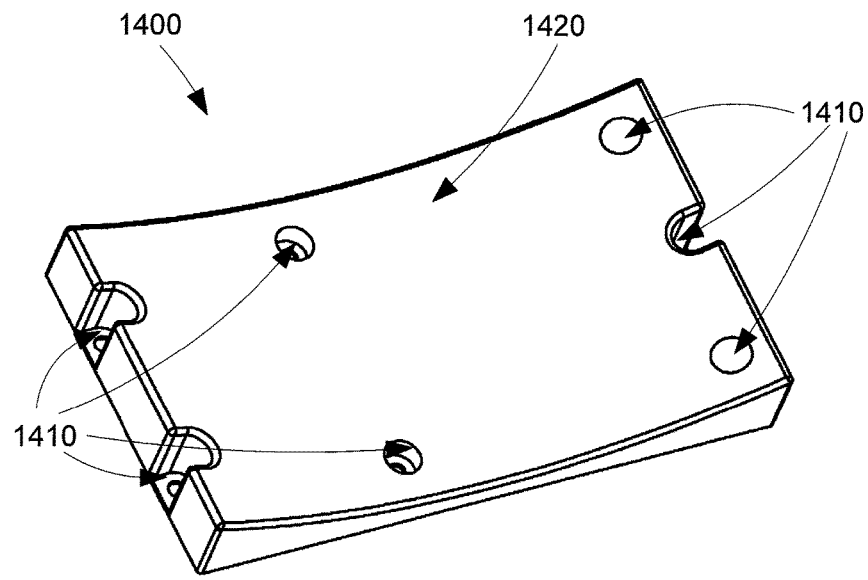
FIG. 14A is a perspective view of a headgear mount to be used with the device of FIG. 3.
Figure 14B:
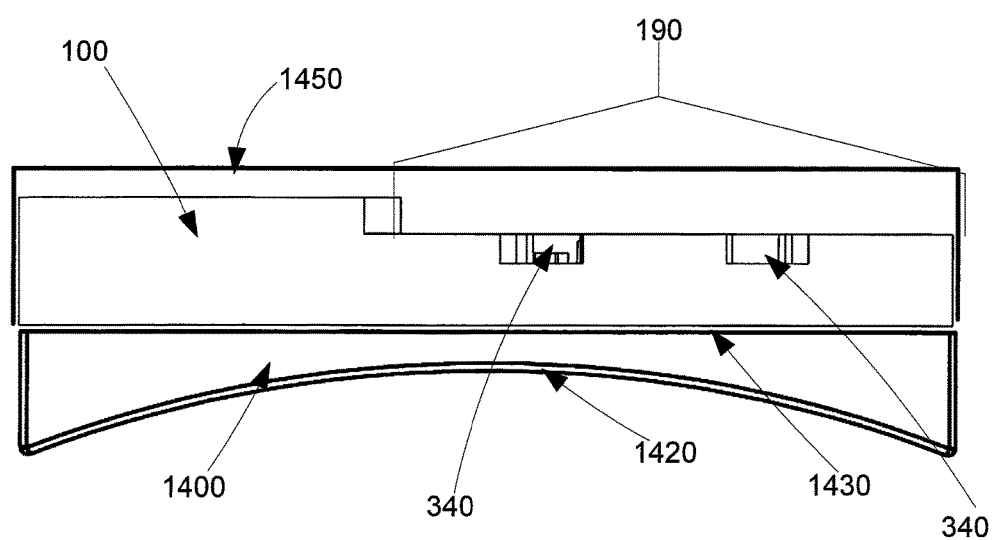
FIG. 14B is a cross-sectional view of the device of FIG. 3 attached to the headgear mount of FIG. 14A.

Back cover 325 may be attached to front cover 320 by way of screws 328, latches, clips or other means. In some embodiments, back cover 325 has an attachment component or means for allowing device 100 to be attached to an article of equipment or clothing or a part of the human body, a vehicle, a building or other structure. For example, the device may be attachable onto a pocket, belt, headgear, arm, leg, or shoulder. In some embodiments, a modular substructure allows device 100 to be able to be attached to a variety of mounting means. FIGS. 14A and 14B illustrate one example mounting means, being a headgear mount 1400. Headgear mount 1400 has a flat surface 1430 for attaching to device 100, and a concave surface 1420 for attaching to an item of headgear. Concave surface 1420 may be a single or double concave surface. Headgear mount 1400 has screw holes 1410 to allow mount 1400 to be attached to device 100.

FIG. 14B also shows a cover 1450 that may be used with device 100. Cover 1450 may fit over device 100 in order to protect it from environmental factors. For example, cover 1450 may reduce the levels of ambient light reaching photodiodes 222 and 224. Cover 1450 may also reduce the likelihood of nodes 200 being displaced from receptors 330. Cover 1450 may furthermore protect device 100 from humidity or dust. Cover 1450 should allow for air to pass through the airflow path of device 100 and nodes 200, and allow for the user to see any status LEDs.

Figure 5:
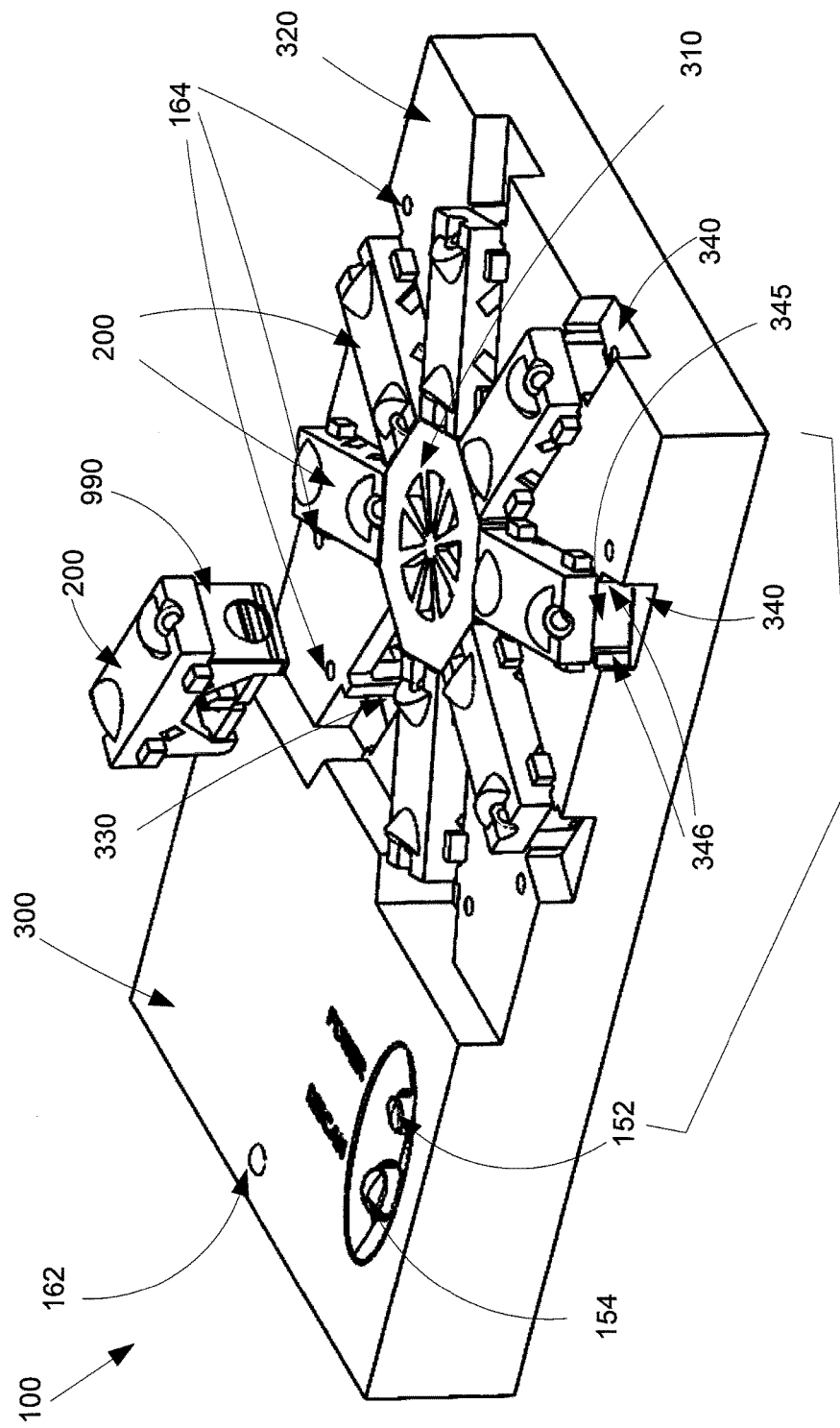
FIG. 5 is a perspective side view of the device of FIG. 3 with a sensing node having been removed.
Figure 6:
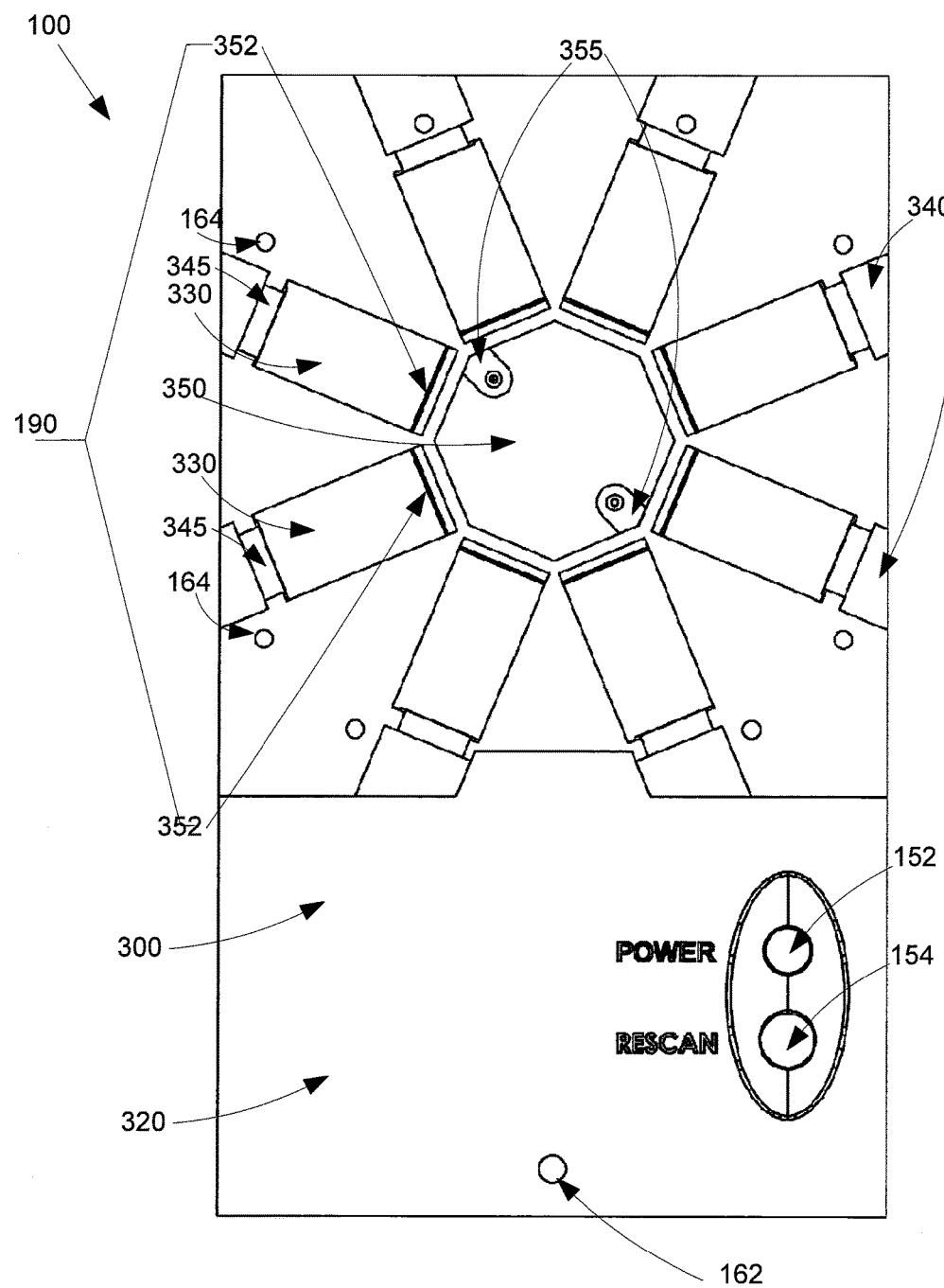
FIG. 6 is a top view of the case of the device of FIG. 3 without the sensing nodes.
Figure 7:
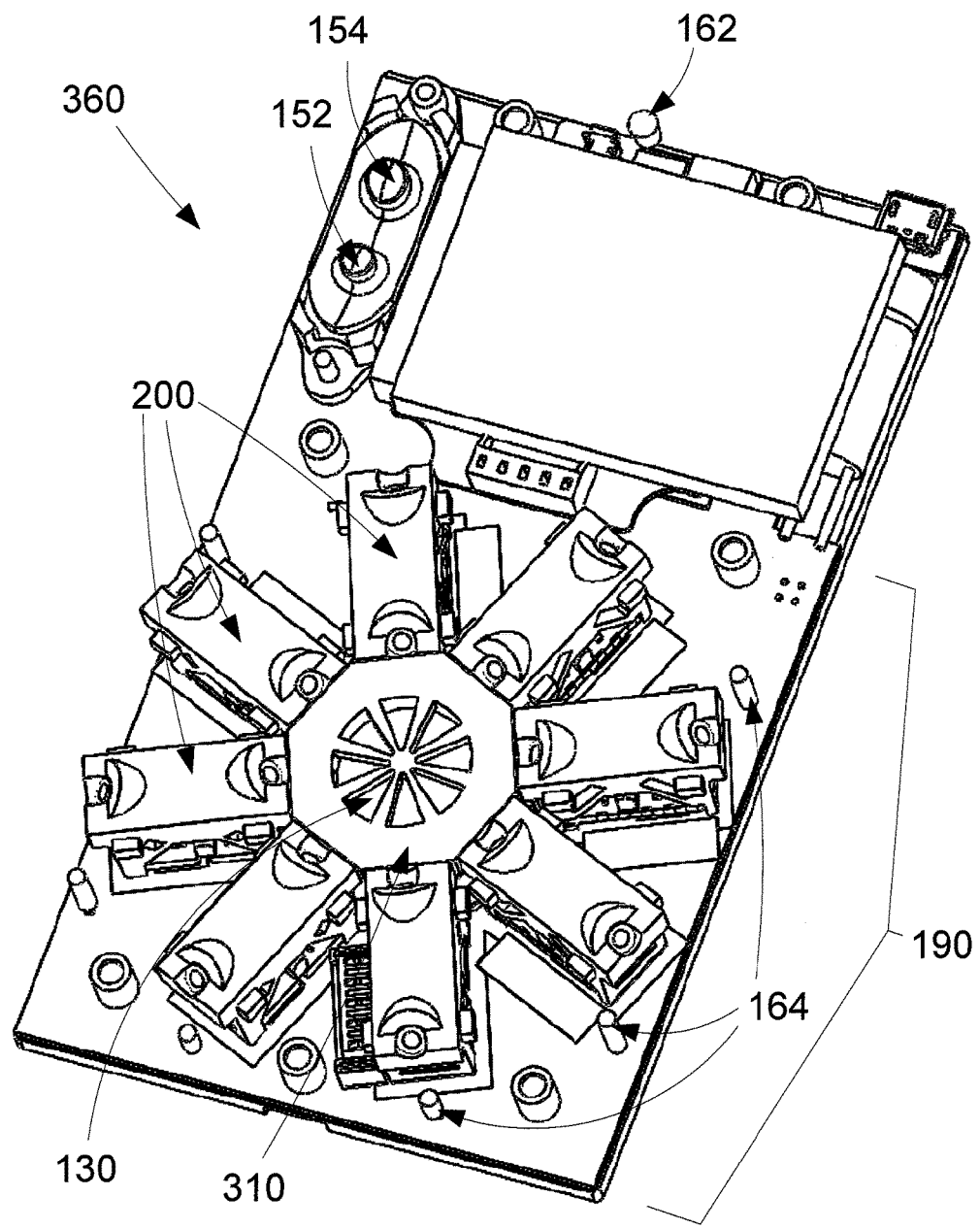
FIG. 7 is a perspective view of the printed circuit board (PCB) of the device of FIG. 3.

FIG. 5 shows device 100 with a sensor node 200 removed. Each sensor node 200 is seated in a sensor node receptor 330, which may be in the form of a recess of a size and shape to receive sensor node 200. Nodes 200 may be held in receptors 330 using node retention components, which may include a system of clips and latches, or by friction or other holding means. In some embodiments, sensor nodes 200 are held in receptors 330 using a sensing component retention mechanism, which may be a clipping system such as spring mounted clipping system 332 (described in more detail below with reference to FIGS. 12 to 13B). One end wall 352 of each receptor 330 is disposed adjacent plenum 350. Plenum 350 is separated from each receptor 330 by wall 352, which has an apertures 354 to allow for fluid communication between the airflow paths of device 100 and sensor nodes 200 (best shown in FIGS. 8 and 12). In some embodiments, sensor nodes 200 may include a seal around the perimeter to engage with the walls of receptor 330 to reduce ambient light entering node 200, and/or reduce unwanted airflow along paths other than paths through node 200. This may be a silicone seal or a rubber seal in some embodiments.

Sensor nodes 200 have a seal 990 which sits tightly against wall 352 when the sensor node 200 is seated in receptor 330 in order to provide a seal between the airflow path of device 100 from fan 130 through aperture 354, and the airflow path through the sensor nodes 200. The second end of receptors 330 are adjacent a vent recess 340, which is separated from receptors 330 by a narrowed neck 345, which is defined by inward vertical projections 346. Projections 346 assist in holding sensor node 200 in receptor 330. Air from fan 130 passes through apertures 354 and through airflow path 420 of each sensor node 200 and out of vent recess 340. The airflow path through device 100 is described in more detail below with reference to FIG. 12.

In some embodiments, device 100 may have an airflow restrictor for equalising the airflow through each aperture 354, even when a receptor 330 is empty or not operative. The airflow restrictor may reduce airflow through a receptor 330 to a level approximately equal to a level of airflow that would occur when a node 200 is received in receptor 330. This may include using an inactive (non-vapour-sensing) node, or an aperture cover or self-closing flap to provide air resistance through aperture 354, being approximately equal to the air resistance created by an active node 200. A self-closing flap may be arranged to partially close over aperture 354 when processor 110 detects that there is no node 200 in the corresponding receptor 330. An inactive node may be a node 200 with no substrate 410, but including electronics to communicate with processor 110 of device 100 to allow processor 110 to recognise that it is an inactive node.

Sensor node receptors 330 contain a signal receiver in communication with processor 110 to receive data signals from node 200 when node 200 is positioned in receptor 330. The signal receiver may include wires connected between processor 110 and a signal coupling portion of device 100.

Figure 8:
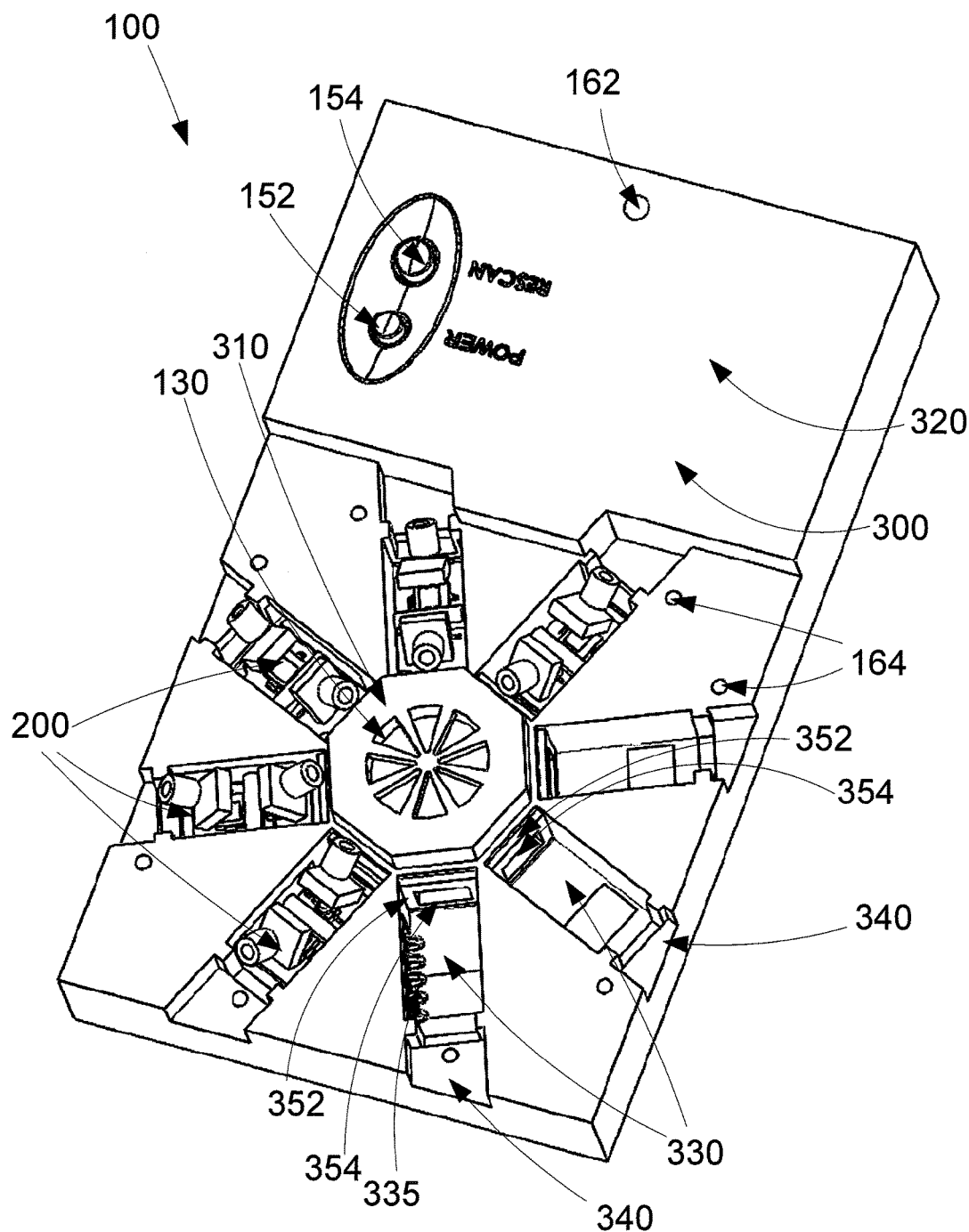
FIG. 8 is a perspective view of the device of FIG. 3 with only one sensing node in place.
Figure 11:
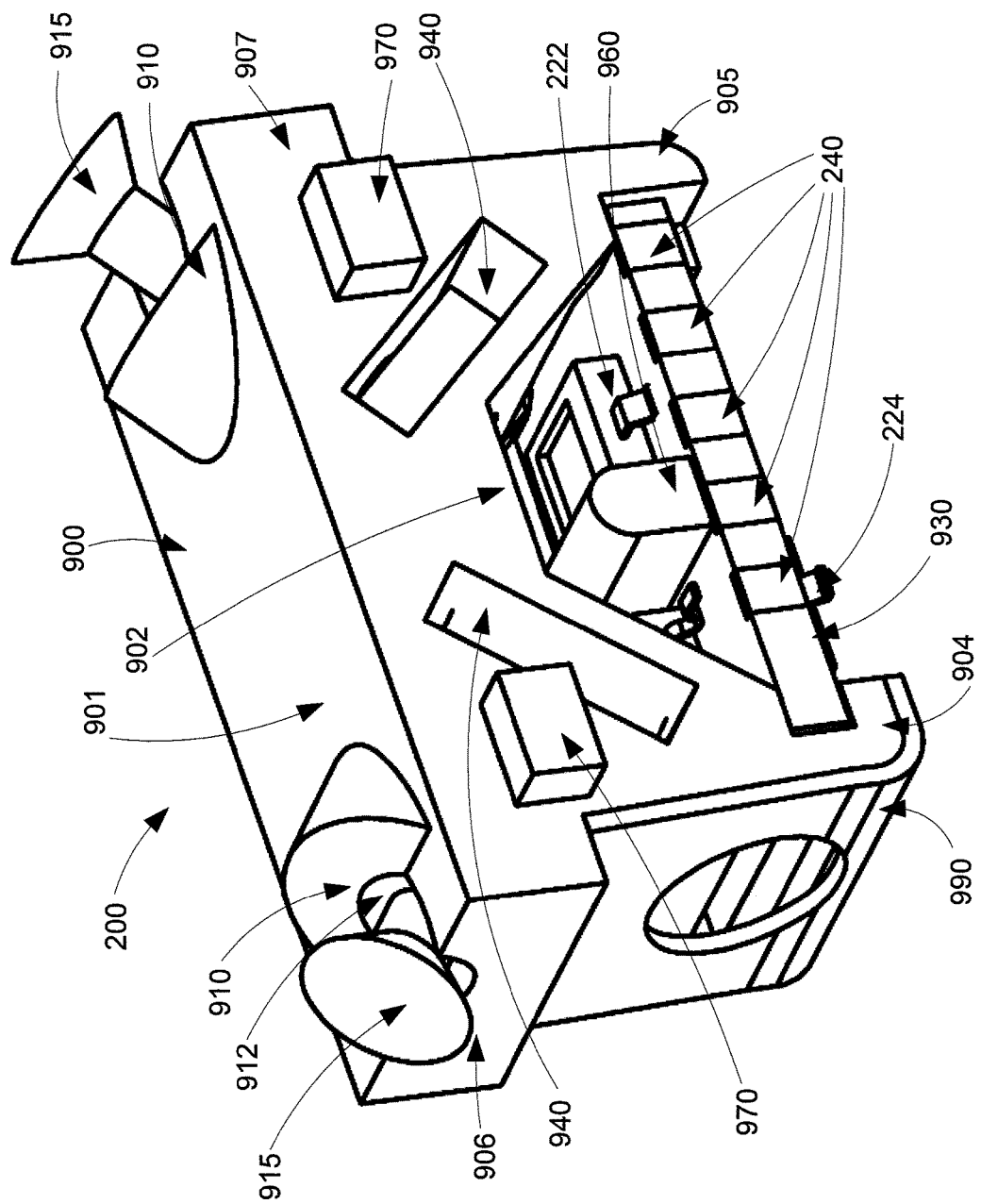
FIG. 11 is a perspective view of a sensing node from FIG. 3 including a PCB and seal.

In some embodiments, the signal coupling portion may include side mounted contacts 335. Side mounted contacts 335 may form electrical contact connections with contacts 240 of sensor nodes 200. In some alternative embodiments, the signal coupling portions may include optical components that communicate with node 200 by optical means, and the signal receiver may include optical fibre. Side mounted contacts 335 are best shown in FIG. 8. Contacts 335 may facilitate electrical signal communications between device 100 and sensor nodes 200, and may allow for the provision of power from power source 170 to sensor nodes 200. In some other embodiments, contacts 335 may facilitate communication by electrical, optical or other means. Contacts 240 may be conductive contacts that may be made of silver, gold, platinum, palladium, or another electrically conductive metal or alloy. Contacts 335 may be gold (or other suitably conductive material) sprung pin contacts, for example, to allow electronic communication between the nodes 200 and the device 100 and provision of power to sensor nodes 200.

FIGS. 9A to 11 show node 200 in greater detail. Node 200 has a housing 900 and a PCB 930 on which the electrical components of sensor node 200 are mounted. Housing 900 is of a size and shape to be received by receptors 330, defining a complementary shaped structure to receptors 330, and in the illustrated embodiments is arranged to take on a table-like shape, with a flat top section 901 and two end leg sections 904 and 905. Top 901 may have overhangs 906 and 907, which may protrude lengthwise beyond legs 904 and 905 on each end of sensor node 200. Overhangs 906 and 907 may be configured to allow sensor node 200 to be easily positioned in a receptor 330 of device 100, and provide a better grip on sensor node 200 when it is being removed from or placed into receptor 330.

Legs 904 and 905 define apertures, optionally in the form of slots 920 and 925, respectively, their outer end walls. Slots 920 and 925 allows for airflow through sensor node 200 via cavity 908. Housing 900 may further have a front wall 902 and back wall 903, which extend from top 901 to part way down legs 904 and 905. Walls 902 and 903 may form an arch between legs 904 or 905, with an interior ceiling 980. Walls 902 and 903 may in some embodiments may define an approximately trapezoidally-shaped void, having angled side edges and a flat top edge. Interior ceiling 980 may be of an A-frame shape, and together with walls 902 and 903 and legs 904 and 905 may define a cavity 908.

Sensor node 200 may have substrate holding portions 940 positioned to span between walls 902 and 903, to hold colour-change substrates 410 in position. Wall 902 may allow access to substrate holding portions 940 to allow substrates 410 to be placed inside. Substrate holding portions 940 may be angled at approximately 90° from one another, following the angled side edges of walls 902 and 903. Ceiling 980 may have apertures 985 providing access to substrate holding portions 940 from cavity 908. When substrates 410 are positioned in substrate holding portions 940, apertures 985 allow for vapours in airflow from cavity 908 to interact with substrates 410. Wall 903 may have pin-holes 945, as shown in FIG. 10D. Pin-holes 945 may be used to remove substrate 410 by applying pressure to it through the pin-holes 945 until substrate 410 is forced out of substrate holding portion 940.

Sensor node 200 may also have screw mount holes 910 extending through top 901 to allow substrates 410 to be adjustably secured to sensor node 200 by screws such as screws 915, which may be nylon screws. Screws 915 are centred around the position of substrate 410, which may not be central to the body of node 200 depending on how substrate 410 is positioned in node 200. Screw mount holes 910 may have brass inserts 912 to provide a screw thread with which the thread of screws 915 can mate. Inserts 912 may be set into node 200 thermally. The screws allow substrate 410 to be held precisely in position, which helps with sensor accuracy by ensuring that the light path between LED 210, substrate 410 and sensor photodiode 222 can be set and is kept to the desired length. Securing substrate 410 with screws may also alleviate issues of increased noise that may occur with rough handling of the device, by preventing substrate 410 from moving with respect to node 200.

Housing 900 may have a series of protrusions 970 formed on walls 902 and 903, that may be used in the positioning and securement of sensor node 200 on device 100. Protrusions 970 may be rectangular in shape, or may be circular, cylindrical, triangular, or of another shape. Protrusions 970 may be configured to align with matched recesses in housing 300 of device 100 to properly position sensor nodes 200 in sensor node receptors 330, or to sit on the upper edge faces adjacent receptors 330 in order to ensure that node 200 is placed at the correct height in receptor 330, and sits flat in receptor 330 rather than tilting. An improperly positioned node 200 may result in restricted airflow as slot 920 may not align with aperture 354. Protrusions 970 may further be configured to reduce ambient light from entering node 200 through cavity 908. In some embodiments, sensor node 200 may have two protrusions 970 on each wall 902 and 903, positioned above substrate holding portions 940, as illustrated in FIGS. 9A to 10C. In some other embodiments, each wall 902 and 903 may have a single protrusion 970, which may be positioned in between substrate holding portions 940, as illustrated in FIG. 10D. In other embodiments, walls 902 and 903 may have three, four, or more protrusions 970, or each wall 902 and 903 may have a different number and/or arrangement of protrusions 970.

Legs 904 and 905 have internally facing PCB holding ridges 950. These allow a PCB 930 to be inserted and held by housing 900. Ridges 950 may be positioned at the bottom of legs 904 and 905, with PCB 930 forming a floor to cavity 908. FIGS. 10A to 10D show node 200 with substrates 410 and PCB 930 with the electronic components in place. PCB 930 holds LED 210, photodiodes 222 and 224, as well as other electronic components such as processor 250. PCB 930 also has an airflow diversion member, such as wall-like barrier 960 situated between LED 210 and sensor 222. Barrier 960 serves to reduce light contamination between LED 210 and sensor 222, and also affects the air flow through node 200 by causing air turbulence, which increases the contact between the air and substrates 410. PCB 930 may also have contacts 240 along one side, to connect to contacts 935 in receiver 330 of device 100 when sensor node 200 is placed in receiver 330, to allow for communication between processor 110 and processor 250.

Substrates 410 may be replaceable and/or disposable, such that a sensor node 200 can be used even after the substrate within it has undergone a reaction, by removing the substrate 410 and replacing it with a fresh one. In order that device 100 can properly detect which chemical vapour was sensed, substrate 410 should only be replaced by an identical substrate that senses for the same chemical vapour. If the properties of the new substrate are changed, ID resistor 230 of the node 200 may need to be changed so that device 200 can properly identify the chemical vapour detected. However, in this case, LED 210 and sensor photodiode 222 may no longer be properly tuned to detect the colour change.

In some other embodiments, node 200 may be a single use, replaceable node. Substrates 410 and/or PCB 930 may be co-moulded into node 200, so that they are not readily removable or replaceable. In such embodiments, screws 915 are not required, as substrate 410 would be held securely within the body of the node 200.

Sensor node 200 may be provided with at least one o-ring or seal such as seal 990. Seal 990 may be placed over slot 920 and integrate with aperture 354 in wall 352 of device 100 when sensor node 200 is positioned in receptor 330, to provide a sealed airflow path from plenum 350 of device 100 and into node 200. Seal 990 may be a replaceable 0.5 mm thick silicon seal glued to the outside of leg 904 of node 200 with a glue such as Loctite 406. One side of seal 990 may be finished with polyolefin primer. For example, a Permabond POP50 cyanoacrylate primer may be used.

When sensor node 200 is placed into a receiver 330 of device 100, seal 990 may compress to allow a tight fit. Seal 990 restricts the amount of air able to leave or enter the airflow path between device 100 and each node 200, to allow for an approximately equal amount of air to be driven through each node 200.

Figure 12:
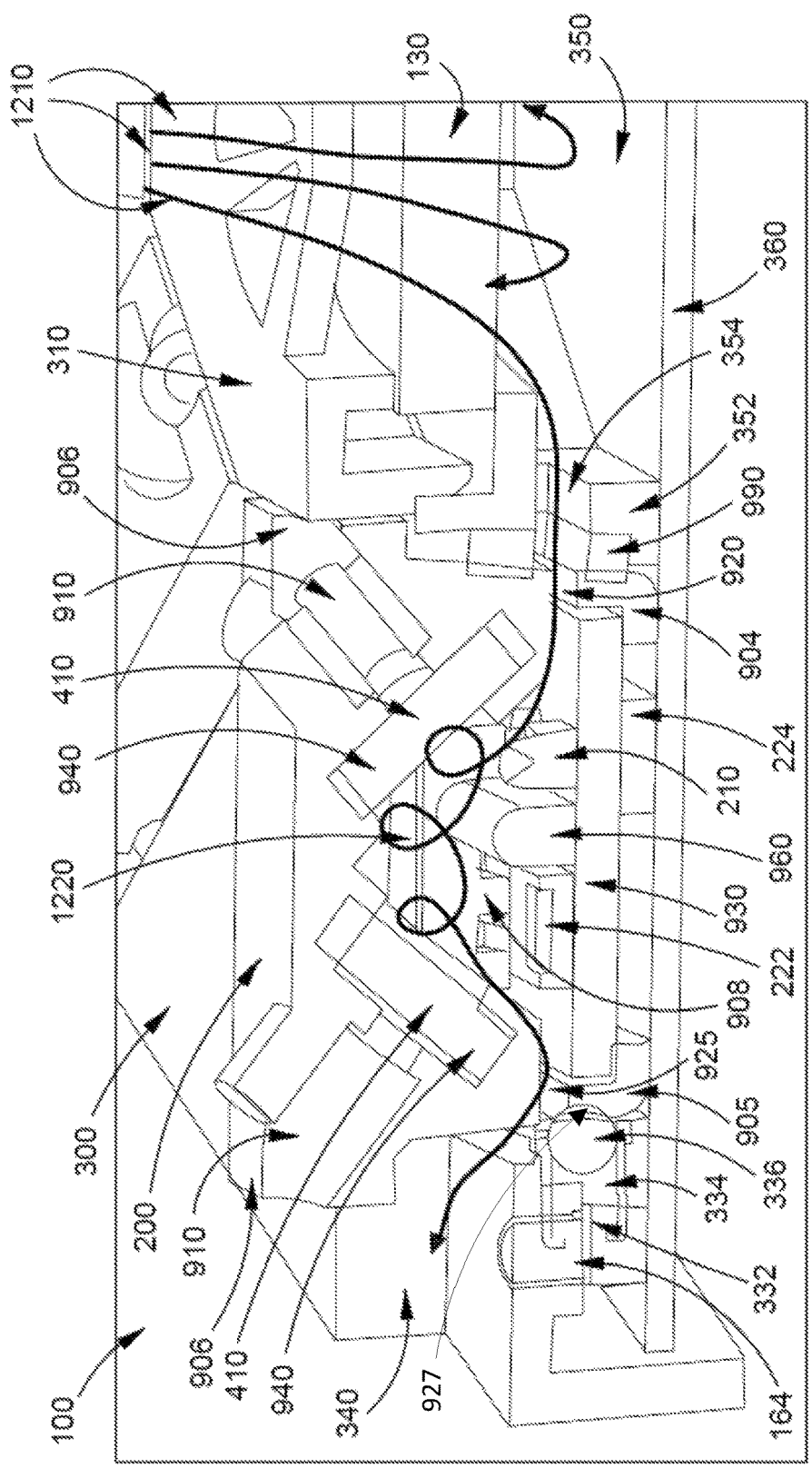
FIG. 12 is a cross-sectional view of the device of FIG. 3 and a sensing node, showing airflow through the device and a sensing node.

FIG. 12 shows the airflow path 1210 through device 100 and a sensor node 200. Air from the environment is drawn through fan cover 310 into plenum 350. Air is then driven by fan 130 through aperture 354 of wall 352, through an aperture in seal 990 and through slot 920 in leg 904 of sensor node 200, into cavity 908 of sensor node 200. As air moves through cavity 908, barrier 960 provides an obstacle for the airflow 1210, causing turbulence 1220. This helps to retain any chemical vapour particles within airflow 1210 and increases the chances of the chemical vapour particles coming in contact with substrates 410. As air is driven into cavity 908 by fan 130, air within the cavity is forced out through vent 925 in leg 904 of sensor node 200, and into recess 340. From recess 340, the airflow path exits device 100 and re-enters the environment within which device 100 is operating.

In some embodiments, filters may be installed over fan cover 310 in order to reduce or inhibit dust, humidity and other particulate matter from entering airflow path 1210 and affecting the function of the optical components. The filters may also or alternatively be bio-aerosol filters, which may be investigated post-use to determine whether there was exposure to any dangerous biological matter, so that treatment can be administered as soon as possible.

Figure 13A:
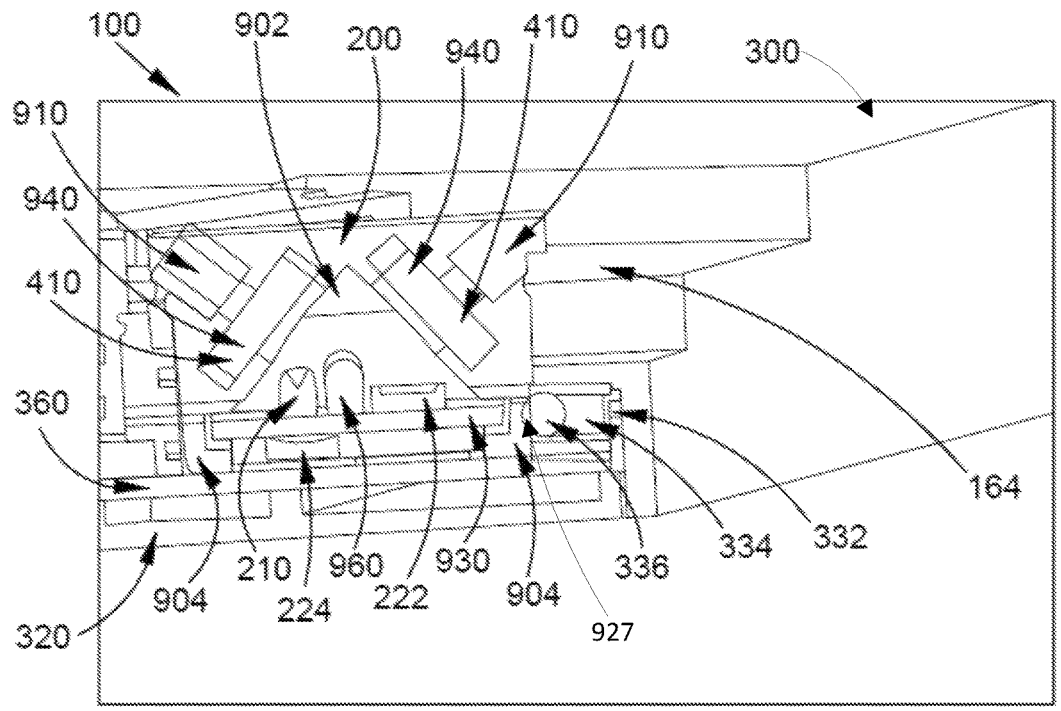
FIG. 13A is a cross-sectional view through the device of FIG. 3 and a sensing node.
Figure 13B:
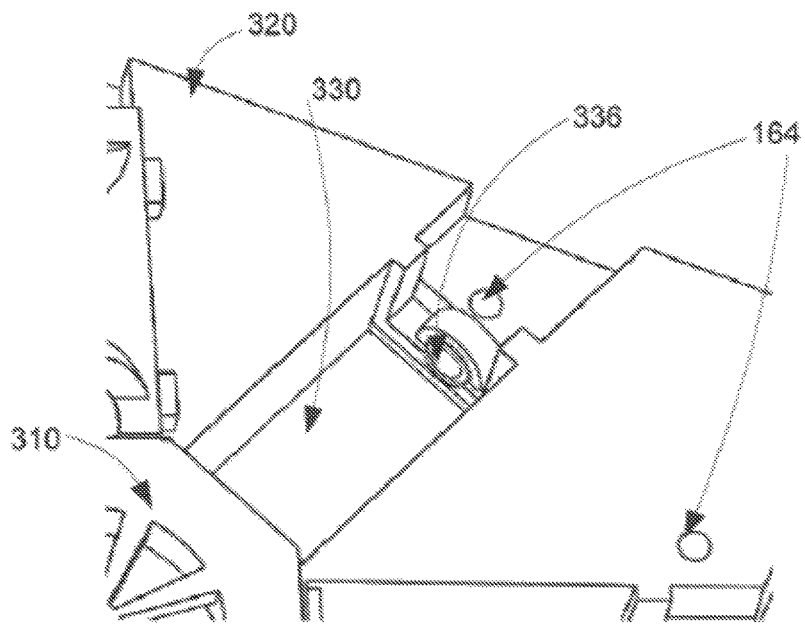
FIG. 13B is a detailed perspective view of a node retention component of the device of FIG. 3.

FIGS. 13A and 13B show spring mounted clipping system 332 in greater detail. Spring mounted clipping system 332 may comprise a spring plunger 334 and a ball 336. Spring plunger 334 may be a metallic compression spring, compressible by a manual force equivalent to a press with the user's finger. Spring plunger 334 may be able to be compressed in order to allow sensor node 200 to be placed into receptor 330, and provide force onto sensor node 200 when sensor node 200 is in receptor 330 adequate to securely hold sensor node 200 in receptor 330. Ball 336 may be a metallic or plastic ball seated in an end of spring plunger 334. Spring plunger 334 may push ball 336 into a depression 927 in leg 905 of sensor node 200. The pressure on sensor node 200 may push sensor node 200 into seal 990, causing seal 990 to compress, and retaining sensor node 200 in receptor 330. Shifting sensor node 200 back against spring mounted clipping system 332 may release the pressure against seal 990, freeing leg 904 of sensor node 200 and allowing sensor node 200 to be lifted out of receptor 330.

Figure 15A:
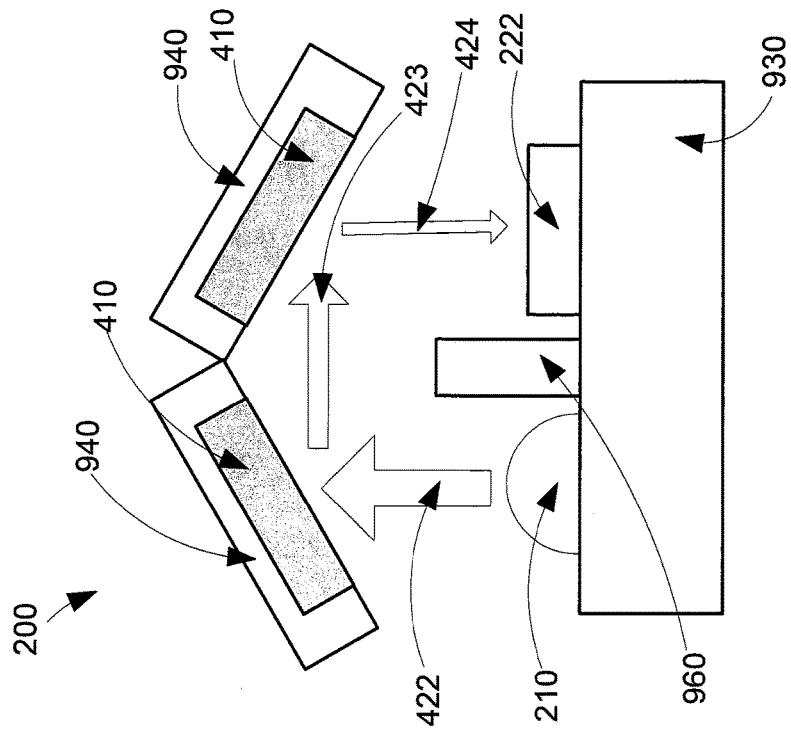
FIG. 15A is a schematic diagram of the light path through a sensing node.
Figure 15B:
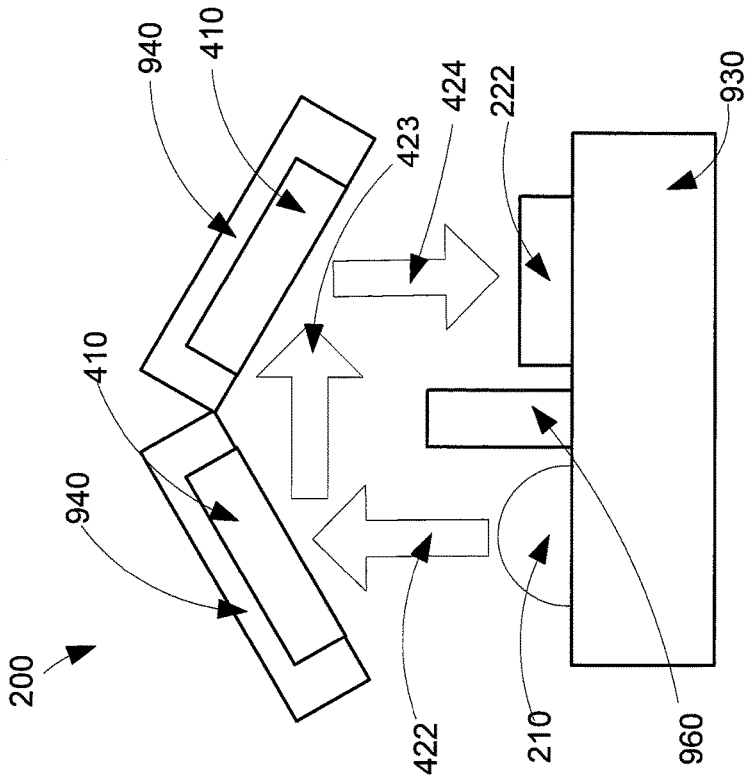
FIG. 15B is a schematic diagram of the light path through a sensing node that has been exposed to chemical vapour.

FIGS. 15A and 15B demonstrate the operation of the sensor nodes 200. FIG. 15A shows a sensor node 200 having a PCB 930 with LED 210, barrier 960 and photodiode 222. Sensor node 100 has substrate holding portions 940 and substrates 410, which have not been in contact with a target chemical. Light 422 is emitted by LED 210, and reflects off substrate 410, which is at an angle to LED 210. The angle may be an angle of between 30° and 60°, and may preferably be an angle of around 45°. Reflected light 423 is then reflected from the second substrate 410. The substrates 410 are separated by an angle of between 60° and 120°, which may preferably be an angle of around 90°. The second reflected light 424 is absorbed by photodiode 222, which produces a voltage based on the light intensity. In some embodiments, a photoresistor or other opto-electrical transducer or sensor may be used, which may produce a change in a current, resistant, impedance, capacitance or inductance based on the light intensity received. The voltage is transmitted to processor 110, which analyses the amount of voltage received to determine whether a colour change has taken place in the substrate 410. In FIG. 15A, substrate 410 is in its unexposed state, shown in the illustrated embodiment as a lighter colour. A light-coloured substrate 410 causes most of light 422 to be reflected, and to reach photodiode 222. This results in a high voltage being produced by photodiode 222, which processor 110 will take to mean there has been no colour-change, and so the target chemical vapour has not been in contact with substrate 410.

In FIG. 15B, substrate 410 has undergone a colour-change reaction, which in the illustrated example has made substrate 410 darker in colour than the substrate shown in FIG. 15A. This results in some of light 422 being absorbed into substrate 410, and only a small amount of light 423 being reflected. Most of light 423 is then absorbed by the second substrate 410, and only a very small amount of the second reflected light 424 is absorbed by photodiode 222. This results in a relatively small amount of voltage being produced by photodiode 222 and a commensurate signal is transmitted to processor 110. Processor 110 determines that this smaller signal means that a colour change has occurred in substrate 410, and so that the target chemical vapour has been in contact with substrate 410. Processor 110 will then cause device 100 to issue an alarm, by activating motor 116 to cause a vibration of device 100, and by causing a change in colour of the respective sensor node LED 164.

As demonstrated by FIG. 15B, having light 422 reflect twice from substrates 410 enhances the sensitivity of sensor node 200, as it causes more light to be absorbed by substrate 410 and increases the reduction of light entering photodiode 222. This subsequently increases the difference in voltage produced by photodiode 222 and received by processor 110, so that processor 110 can more easily distinguish a change in colour in substrate 410. In some embodiments, substrate 410 may be a darker colour in its unexposed state and become relatively lighter after a colour-change reaction, resulting in an increase in reflected light. In this case, FIG. 15B would show the scenario before a reaction had occurred, while FIG. 15A would show the result when a chemical vapour had come into contact with substrate 410. In this case, the double reflection would produce an increase in the light reflected.

When a node 200 is placed into receiver 330 of device 100, a connection is formed between sensor node 200 and device 100 through contacts 335 and 240. If device 100 is powered on, processor 110 will be able to initiate communications with processor 250 in order to identify, initiate and calibrate sensor node 200. The process of calibrating sensor node 200 is shown flowchart 1600 of FIG. 16. At 1610, processor 110 automatically detects that a sensor node 200 is located in a receptor 330. This may be due to a signal sent by sensor node processor 250, or through other means, such as by closing of a circuit, recognising a connection or shorting of contacts 335. When a node 200 is detected as being present in a particular receptor 330, processor 110 may send signals to a correspondingly positioned sensor node LED 164 in order to cause LED 164 to shine a green light adjacent that receptor 330, for example.

At 1620, processor 110 identifies the type of the detected node 200 by receiving identification data from node 200, which may be received via ID member 230. Processor 110 may measure an identification resistor, or read a value from a memory unit on sensor node 200, for example, in order to determine the vapour sensor type of the node 200. In other embodiments, processor 110 may perform a handshake routine with processor 250, by which it may be able to identify the node type. When processor 110 has identified node 200, it stores the node type in memory 120, along with the position of node 200 in the sensor bank 190. Any settings associated with the node (vapour sensor) type are adjusted, such as the threshold values of voltage supplied by photodiode 222 of sensor node 200 used to determine whether substrate 410 has experienced a colour change.

At 1630, automatic calibration of node 200 begins, which may involve processor 110 calibrating at least one setting of node 200. This may be done by a node reading taken by measuring the output of photodiode 222 based on various levels of light emitted by LED 210. For example, in some embodiments LED 210 may be flashed on at full power and then turned off multiple times rapidly in succession. The output of photodiode 222 may be measured during both the on and off stages, and the maximum and minimum intensities measured may be compared at 1640 to a window of intensity values that indicate that there isn't overexposure or underexposure, and that the values are within the window of values A/D converter 180 can operate between, which may be +/−64,000 units for a 16 bit A/D converter. If the values are within the window, calibration is completed at 1645, and memory 120 is updated by processor 110 to indicate that node 200 is calibrated. Calibration may be used to account for slight changes in each individual substrate 410, such as slight variations in the original colour of the substrate 410.

If the values are outside the window at 1640, processor 110 may attempt to adjust the limits of A/D converter 180 to a range that would fit the measured values. If this can be achieved at 1655, processor 110 restarts calibration at step 1630. If the A/D converter operating window cannot be translated to fit both the upper and lower intensity values, processor 110 adjusts the signal gain supplied to LED 210 so that the intensity is dropped at 1665, and the calibration process is repeated from step 1630. If the gain cannot successfully be adjusted to fit the working window of A/D converter 180, calibration is stopped at 1670 and processor 110 updates memory 120 to indicate that the node 200 was unable to calibrate correctly. This calibration routine ensures that a maximum sensitivity of nodes 200 is achieved.

A method of operation of device 100 is illustrated with reference to flowchart 1700 in FIG. 17. Device 100 may start up at 1705 when a user presses power button 152.

This may cause power supply 170 to supply power to processor 110 as well as other components. Processor 110 may indicate that it has been started up by sending activating commands to output components 160, which may cause status LED 162 to turn on, for example, or cause motor 166 to be activated and cause vibration of device 100. Processor 110 may then attempt to communicate with processors 250 of sensor nodes 200 at step 1710. Processor 110 may try to identify sensor node 200 by ID member 230 at step 1715, which may include measuring an ID resistor value, or performing a handshake with processor 250. Processor 110 may also retrieve data from each node 200. In some embodiments, the data may include a node type of the node 200. The processor may then store the node type in memory 120 along with the position of node 200 in sensor bank 190. Processor 110 may retrieve alarm trigger conditions and cross-reactivity of data pre-stored in memory 120 for each node type. Alternatively, in some embodiments the data read from each sensor node 200 may include alarm trigger conditions, and cross-reactivity data of the substrate 410. Alarm trigger conditions may be used by processor 110 to determine whether node 200 has detected a chemical vapour. Cross-reactivity data may indicate how sensor node 200 responds to various target gases. Processor 110 may use the collected data to compile a look-up table for use in the deconvolution process at step 1760, described below.

Processor 110 may then activate some output to indicate to the user which nodes have been identified. For example, processor 110 may send signals to appropriate sensor node LED 164 to turn it green. At 1720, if the user observes that any engaged nodes 200 have not been detected, they may initiate a rescan of nodes by pressing rescan button 154. Processor 110 responds to a signal from rescan button 154 by repeating the steps from 1710. If the user does not press the rescan button, processor 110 does not receive a rescan signal and assumes that all of the nodes plugged in have been detected.

Figure 16:
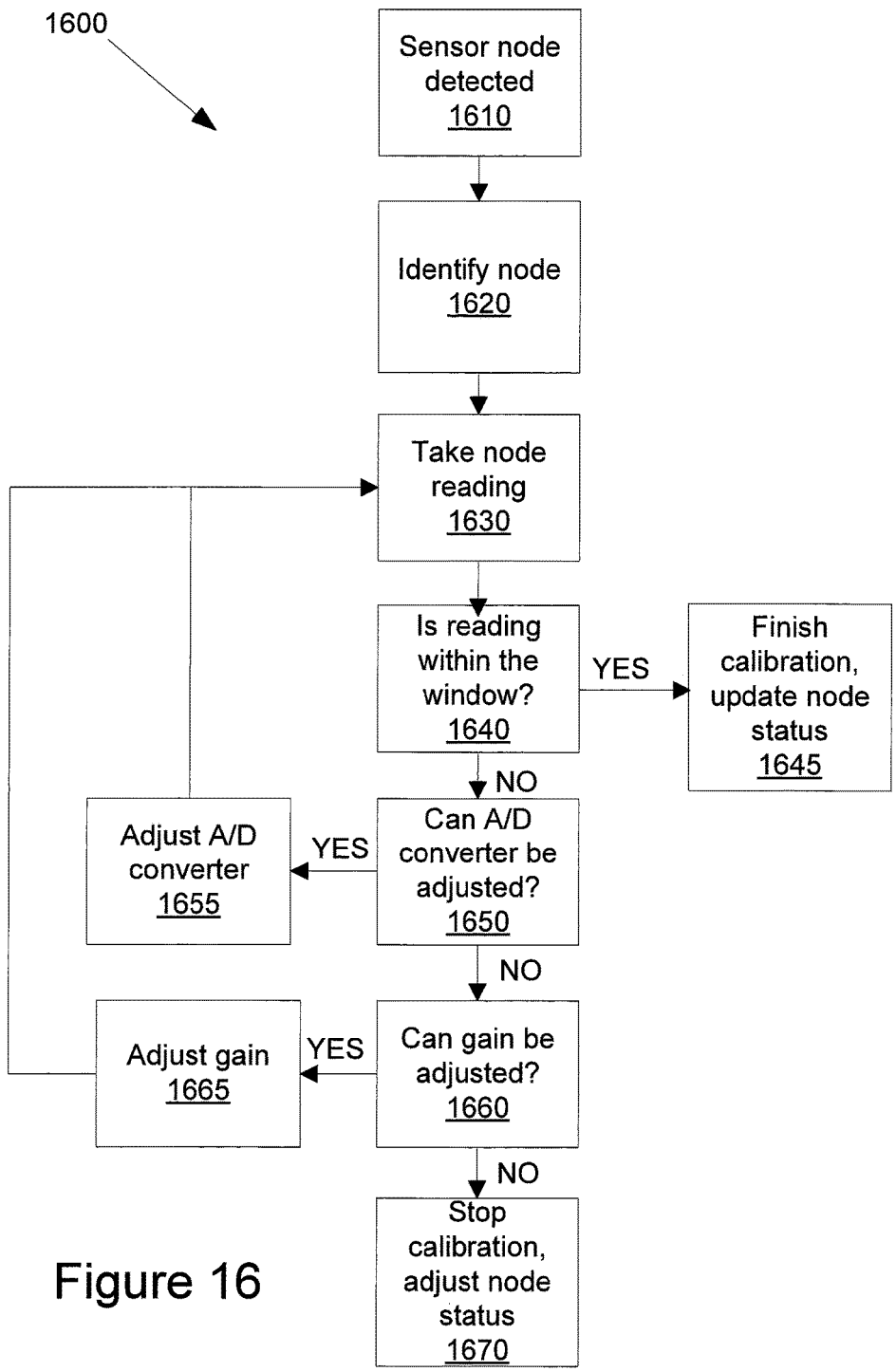
FIG. 16 is a flowchart of a sensing node calibration process.

Once the nodes 200 are detected, they automatically calibrate at step 1600, as per flowchart 1600 in FIG. 16. At 1730, each node 200 begins continually and regularly sampling for the specific target vapour it is calibrated to detect. Sampling may occur at a frequency of once every 30 seconds to a frequency of 30 times per second. For example, sampling may occur every 5, 10, 15, 20, 25 or 30 seconds, or sampling may occur at a frequency of 5, 10, 15, 20, 25 or 30 samples per second. In some embodiments, a frequency of one sample per second may be used. Processor 110 runs fan 130 to continually supply air to sensor nodes 200, and activates LED 210 to emit light onto substrate 410. Photodiode 222 continually produces a voltage corresponding to the light levels that it receives, which is sent by processor 250 to processor 110 via A/D converter 180. LED 210 may emit light at a level below that of the maximum level of light intensity determined by calibration step 1600, to ensure any variation does not cause overexposure of the A/D converter's maximum range. For example, LED 210 may emit light at between 70% and 90% of the maximum intensity value, which may preferably be around 80% of the maximum intensity value in some embodiments.

When a device 100 is exposed to a target chemical vapour, the vapour may be driven by fan 130 into sensor nodes 200. The vapour may contact substrates 410. If a target chemical vapour makes contact with a corresponding substrate 410, substrate 410 may chemically react with the vapour, producing a colour change in substrate 410. A colour change in substrate 410 may affect the light received by photodiode 222, as it will affect the light reflected from LED 210 into photodiode 222. A change in light received by photodiode 222 may result in a change in voltage produced by photodiode 222. The signal output of photodiode 222 is received by processor 110 via the A/D converter.

If no change in the light intensity as determined by the voltage produced by photodiode 222 is detected by processor 110, processor 110 continues to sample, by running fan 130, LED 210 and photodiode 222 at step 1745. Processor 110 continually calculates the rate of change, or the gradient, of the signal received from photodiode 222. An alarm is automatically triggered by processor 110 at 1750 only if the light intensity and the gradient of the light intensity detected by sensor 222, as determined by the voltage output by photodiode 222 and interpreted by processor 110, both fall outside of a specified tolerance and alarm trigger conditions for the node 200 as determined at step 1715.

Device 100 may be configured to automatically trigger an alarm when the target chemical reaches a pre-set level as determined by processor 110 based on the alarm trigger conditions. The level may be set electronically to a level at or below which the target chemical is harmful to humans, for example. In some embodiments, intensity changes of +/−5% and gradient changes of +−0.05 may be set as the tolerance levels that trigger the alarm. This is determined by processor 110 by tracking the signal produced by photodiode 222, and determining a rate of change or gradient for the intensity received. In some embodiments, the change in gradient of the intensity of the signal from photodiode 222 is calculated using a moving 30 second window, by comparing the data points captured at the 0 second and 30 second marks. Processor 110 may be configured to monitor the values of the data signals produced by photodiode 222 and to determine that a first alarm condition has been met when the values reach a first predetermined threshold. Processor 110 may further be configured to analyse the rate of change of the data signals produced by photodiode 222 and to determine that a second alarm condition has been met when the values reach a second predetermined threshold.

The response time of device 100 between being exposed to a target gas and for processor 110 to determine that a value determined from the signal output of photodiode 222 has reached a predetermined threshold may be in the order of several minutes or several seconds. The response time may be around 10, 20, 30, 40, or 50 seconds in some embodiments, or the response time may be around 1, 2, 3, 4, 5, 6, 7, 8, 9, 10 minutes. In some embodiments, the response time may be between 5 to 10 seconds.

Sensing for both a drop in light intensity and the gradient or rate of change of the signal provides for more accurate sensing than using the light intensity alone, as it accounts for any signal drift over time. As seen in graph 1900 of FIG. 19, when a target vapour is introduced to the sensing environment, the intensity response 1910 of the respective sensing node 200 drops significantly, compared to signal 1920 from a second sensing node 200, which is merely experiencing drift. If the alarm were triggered based on the level of signal response, it can be seen that signal 1920 may eventually trigger the alarm, as it may drift below the designated level, despite not sensing its respective target chemical vapour. Therefore, processor 110 may be configured to generate an alarm output only when the first and second alarm conditions have been met.

When processor 110 determines that a gas has been detected by sensor node 200 at 1750, processor 110 may activate indication components such as output components 160 to indicate the detection of a chemical vapour to the user. The indication components may be audible, visual and/or tactile components. In some embodiments, processor 110 may cause device 100 to vibrate by activating motor 166 to notify the user of an event, and may cause node LED 164 corresponding to the node 200 that was triggered (i.e. by detecting its target vapour) to turn red. Processor 110 may compile a list of triggered nodes in memory 120 for future use by recording the identification data of any nodes 200 that are triggered. The device may also store information such as the time at which the node was triggered, and may monitor the triggered node 200 to determine how strongly substrate 410 reacted to the chemical vapour, such as by recording the maximum intensity of the signal received from node 200, or the rate of change of the signal over time. In some embodiments, device 100 may then continue to vibrate one or more times every interval (e.g. 60 seconds) for a number (e.g. 5) of times after the initial node 200 was triggered. In some embodiments, device 100 may continue to monitor the nodes for a predetermined time period, which may be less than 10 minutes, and may be 20, 30, 40 or 50 seconds, or 1, 2, 3, 4, 5, 6, 7, 8, 9, or 10 minutes, for example. In some embodiments, the time period may be between 10 seconds and 5 minutes, and in some embodiments the time period may be around 1 minute.

At 1760, processor 110 may determine whether more than one node 200 was triggered by reading the list of triggered nodes stored in memory 120. If processor 110 determines that more than one set nodes 200 was triggered, processor 110 may automatically perform disambiguation or deconvolution calculations to determine which target gas was actually sensed. As substrates 410 may exhibit cross-reactivity with multiple chemicals, a node 200 may be triggered by a chemical vapour that is not its target chemical vapour. A target gas may cause reactions in several different substrates, or nodes may produce false positive readings due to background contaminants present in the test environment, and so a single gas may trigger multiple sensor nodes 200. Using multiple data streams allows for the detected gas to be identified more accurately than simply using the data from a single substrate.

A disambiguation table (such as the example table 1800 which is shown in FIG. 18) may be used by the device to determine which gas was detected by deconvoluting the data streams from multiple nodes 200. The combination of triggered nodes 200 is compared to the "Responding nodes" column 1820 in the table. A particular combination will generally correspond to a single target gas or chemical class in the "Target gas" row 1810. In the example table 1800, a combination of hydrogen sulphide, hydrogen cyanide and phosphine sensitive nodes 200 being triggered corresponds to hydrogen sulphide being detected, for example. A combination of hydrogen cyanide and phosphine sensitive nodes 200 being triggered corresponds to phosphine being detected. In some embodiments, where multiple devices 100 are being used in a close proximity and communicating between each other, devices 100 may allow for deconvolution across all of the triggered nodes in all of the devices 100 in communication. In some embodiments, processor 110 may also use additional data stored in memory 120, such as the order in which the nodes were triggered, or how strongly substrates 410 reacted to the vapour, to further increase the specificity with which the target vapour can be identified.

Figure 17:
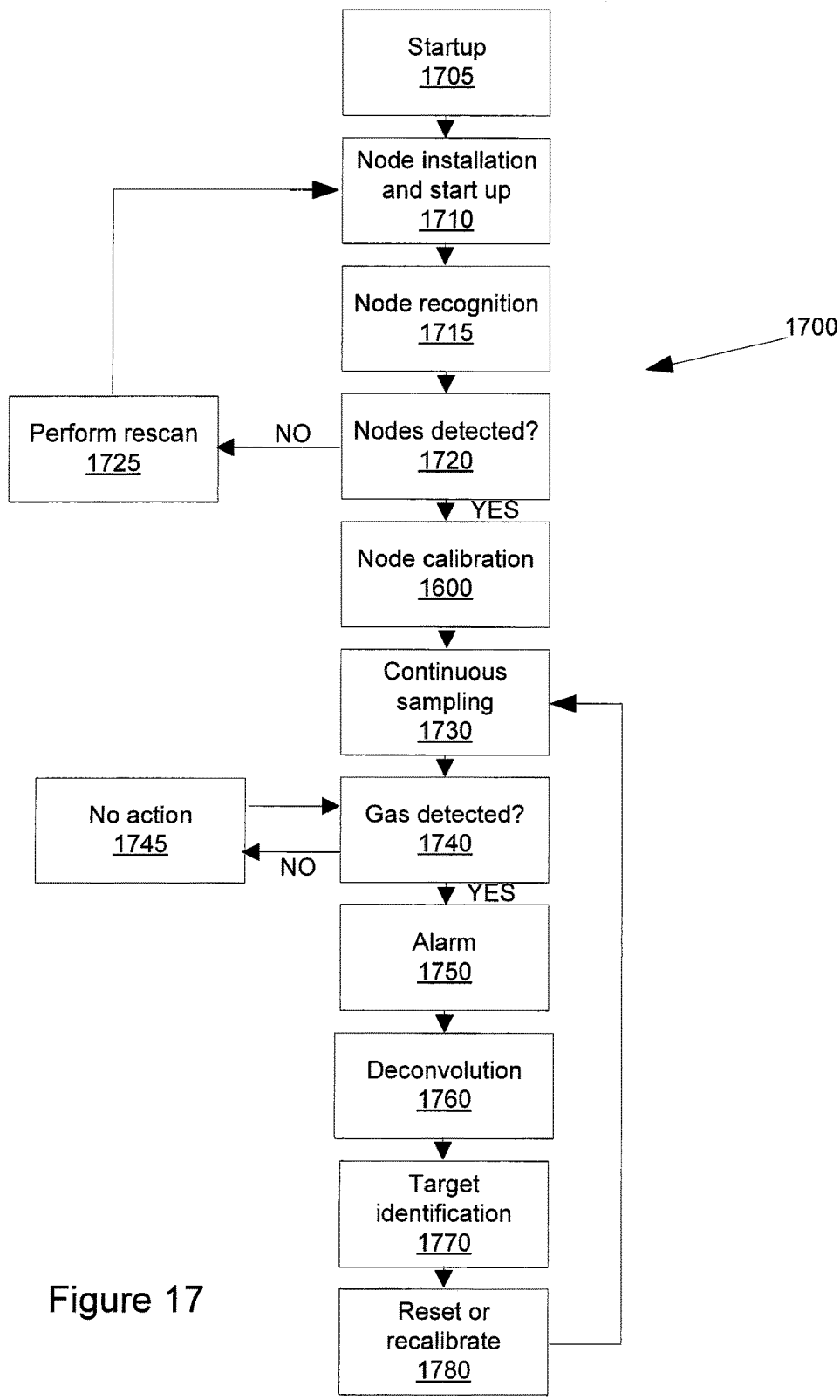
FIG. 17 is a flowchart of the operation of the device of FIG. 3.
Figure 19:
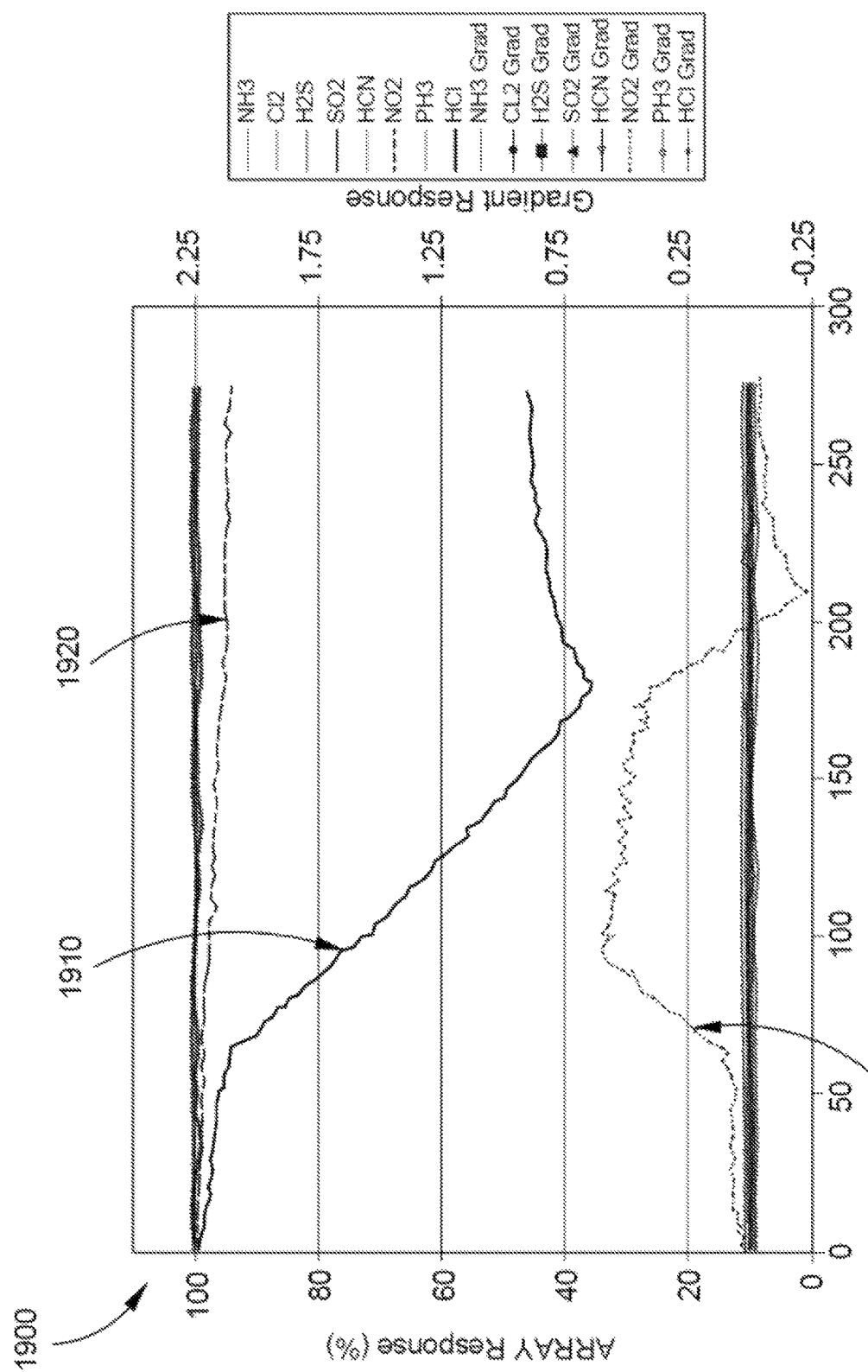
FIG. 19 is a graph showing the intensity and gradient response of a selection of sensor nodes.

In the illustrated method shown in FIG. 17, processor 110 calculates the target gas detected using an internal lookup table stored in memory 120. This may take approximately 60 seconds in some embodiments. At 1770, processor 110 may activate further output components 160 to display the target gas detected to the user. For example, in some embodiments, processor 110 may activate signals to cause the LED 164 corresponding to the target gas sensitive node 200 to turn red, and may cause motor 166 to vibrate device 100. Some embodiments may alert the user by further alarm mechanisms, such as other optical or audible protocols. An audible alarm may sound, or the data may be displayed on a screen, for example. Sensor nodes 200 may be labelled in a way such that a user looking at the device will be able to tell what chemical was detected based on the LED 164 that turned red. They may have a human-readable label identifying the target vapour, for example. In other embodiments, the user may be notified of the identified gas by a different means, which may be visual or non-visual. For example, identification information corresponding to the identified vapour may be displayed on a screen on device 100 or played through a speaker on device 100. In some embodiments, the information may be sent by device 100 to be displayed on a headset or heads-up display, or played through headphones designed to be worn by the user. In further embodiments, motor 166 may be caused to vibrate device 100 in a specific vibration pattern to allow the user of device 100 to identify the detected gas by tactile means. The vibrations may spell out the name of the chemical vapour in Morse code, for example, or the vibrations may otherwise correspond to a unique node 200 carried by device 100.

In some embodiments, the user may be able to perform a two stage scan. After a gas is detected, the user may press rescan button 154 to reset nodes 200 to an untriggered state. Nodes recalibrate at 1600 and proceed to sense for gases at 1730, following steps 1740 to 1770. If substrate 410 has not completely changed colour, device 100 may be able to sense for further gases by detecting for a further colour change in that node 200. Some substrates may quickly be exhausted and so be unsuitable for continued use to sense a second time.

In some embodiments, device 100 may also communicate with other devices 100 to send and receive information about detected chemical vapours. Several devices 100 may share identification data of any nodes 200 that are triggered, for example, so that a bigger lookup table can be generated and chemical vapours can be identified more accurately by each device 100.

Figure 24:
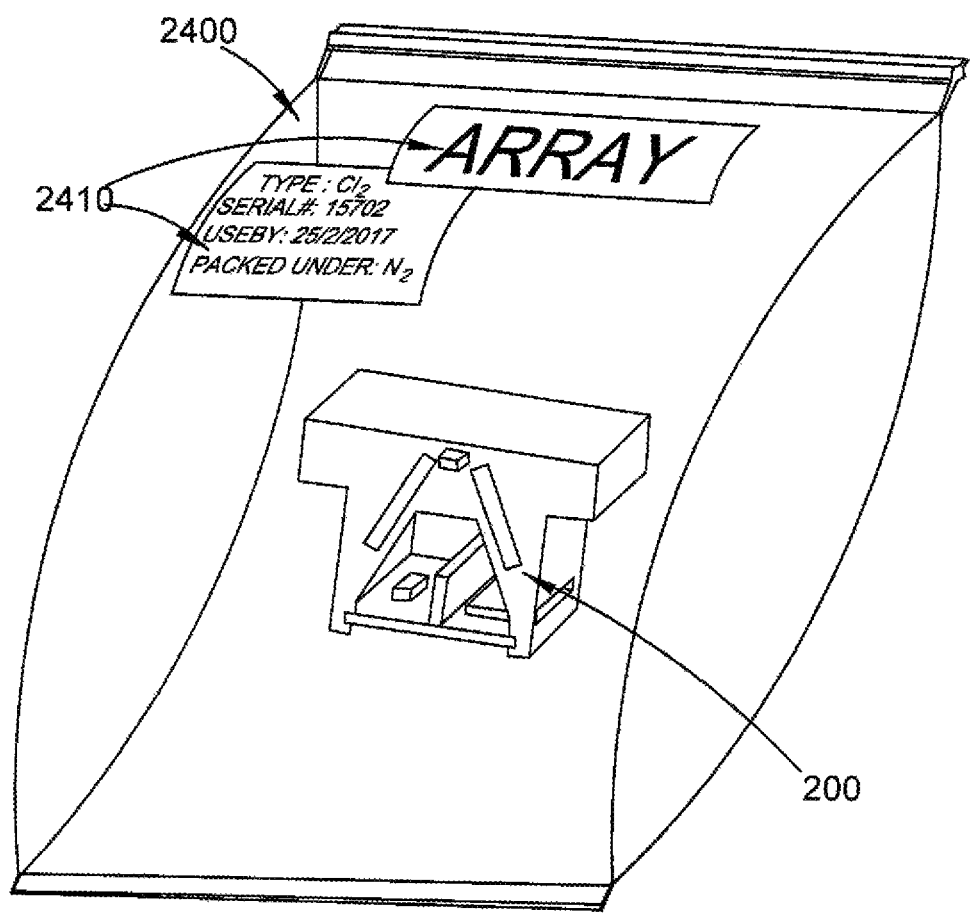
FIG. 24 is a perspective view of a sensing node in packaging.

As shown in FIG. 24, nodes 200 may be provided in packaging 2400 to protect them from environmental conditions before use. They may be packaged based on the specific chemical qualities of the substrate 410. For example, some forms of packaging 2400 may need to be opaque to reduce the deterioration of substrates 410 due to being bleached by light. In other embodiments, packaging may be impermeable, and contain a specific packaging gas at a humidity level that will slow the deterioration of substrate 410. Packaging 2400 may have labels 2410 which may provide information to the user, such as: the name of the node; the type of vapour the node detects; a serial number of the node; a use-by date after which the substrate is considered to have deteriorated to an extent that makes it unreliable; the packaging conditions such as the gas the node is packed in; and other information.

Figure 25:
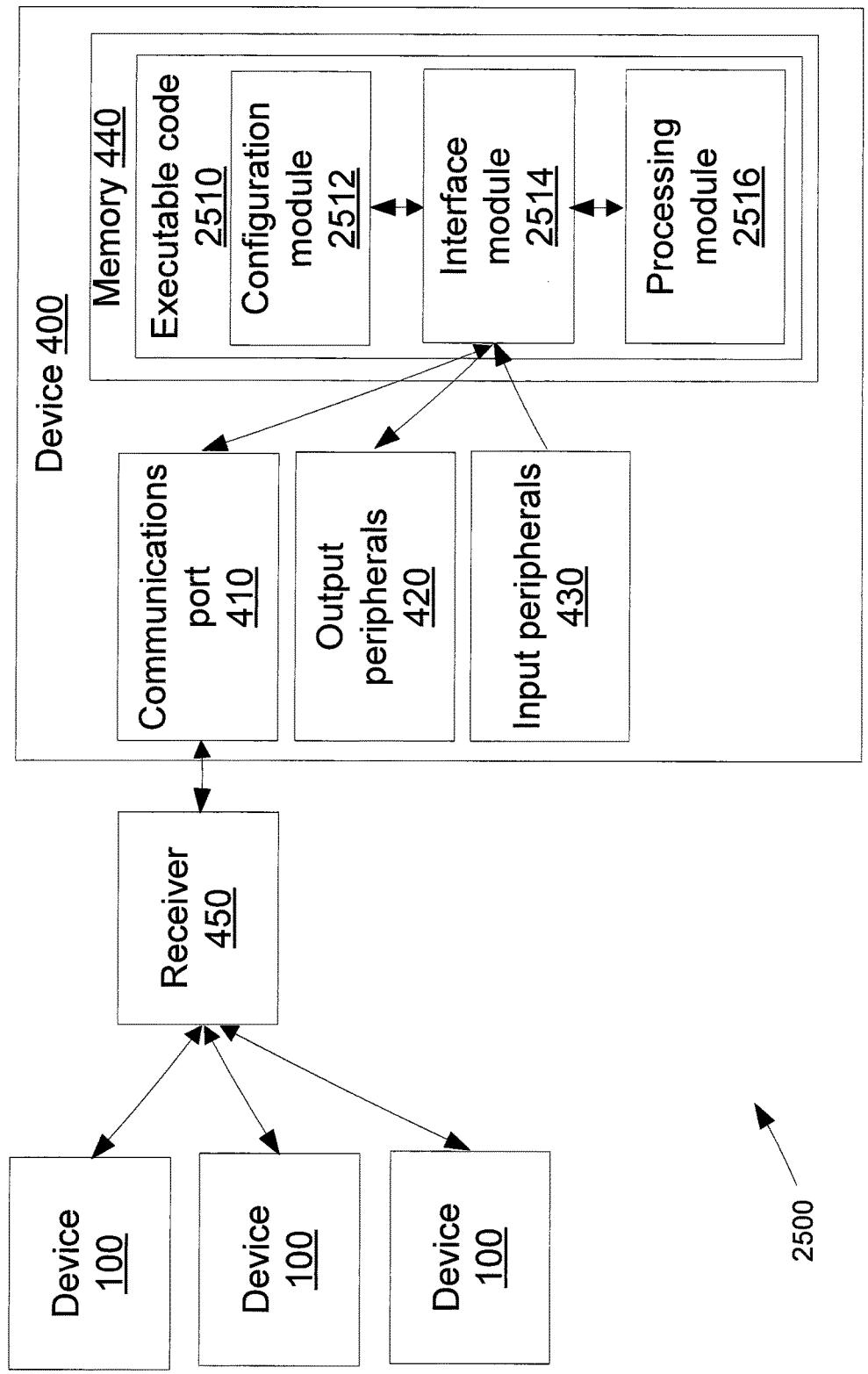
FIG. 25 is a block diagram of executable code running on a computing device in communication with a plurality of devices of FIG. 1.

FIG. 25 is a block diagram 2500 showing the interactions between device 100 and device 400. Device 400 may have a communications port 410, output peripherals 420, input peripherals 430, and memory 440 storing executable code 2510. Executable code 2510 may contain code modules, such as a configuration module 2512, an interface module 2514, and a processing module 2516. Interface module 2514 of executable code 2510 may be configured to receive information 2520 from a communications port 410 of device 400, which may be in communication with one or more devices 100 through receiver 450. Interface module 2514 may communicate this data to processing module 2516, which may then be able to generate output data, and communicate this data back through interface module 2514 to output peripherals 420 of computing device 400. Interface module 2514 may cause the data to be displayed on a screen of computing device 400, or to play through audio speakers (not shown) of device 400, for example. Information received by interface module 2514 from device 100 may include a geographical position of device 100, whether nodes 200 of device 100 have been triggered by detection of their target vapour, and any other outputs from sensors on device 100, such as temperature, humidity, or measured vital signs of the user of device 100.

Executable code 2510 may allow a user to track multiple devices 100 on a map, and alert them through audio and/or visual means when a vapour is detected by any of the devices 100. It may be able to plot the area in which the detection occurred on the map, and to identify the vapour or vapours detected. In some embodiments, configuration module 2512 may be configured to generate data and to cause this data to be communicated back to devices 100 by interface module 2514. This data may be generated through user input through input peripherals 430 of device 400 in some embodiments. Data communicated to devices 100 by configuration module 2512 may include data that affects the way in which devices 10 operate. For example, the data may include commands to alter the sensitivity or filtering of device 100, or to update data stored in memory 120 of device 100. For example, configuration module 2512 may produce data to cause an internal lookup table used for deconvolution by device 100 to be updated.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A sensing component for sensing chemical vapours, comprising:
   a housing defining an airflow path, the housing further defining a complementary shaped structure configured to be received in a receptor of a carrier device;
   a light emitting component;
   a first substrate positioned so that vapours flowing along the airflow path can contact the first substrate, wherein at least one property of the first substrate changes when it comes into contact with a target vapour, the first substrate also positioned to receive and reflect light emitted by the light emitting component;
   a second substrate positioned so that vapours flowing along the airflow path can contact the second substrate, wherein at least one property of the second substrate changes when it comes into contact with a target vapour, the second substrate also positioned to receive and reflect light reflected by the first substrate;
   a sensing element positioned to receive light from the second substrate, the element being configured to detect a change of the at least one property of at least one of the first substrate and the second substrate and to produce a signal based on the detected change; and
   a signal coupling portion to allow output of output signals based on the produced signal to the carrier device;
   wherein the sensing component is configured to be manually insertable into the receptor and manually removable from the receptor.

2. The component of claim 1, further comprising an airflow diversion member positioned in relation to the airflow path to induce air turbulence within the housing wherein the airflow diversion member is positioned to promote airflow towards the substrate.

3. The component of claim 1, further comprising identification circuitry to allow the component to be identified electronically, wherein the identification circuitry comprises an electronic component having a predetermined value to act as an identifier of the sensing component.

4. The component of claim 1, wherein the light emitting component is tuneable to emit a pre-determined wavelength of light.

5. The component of claim 4, wherein the sensing element is a photo-sensitive element tuneable to detect a pre-determined wavelength of light.

6. The component of claim 4, further comprising a calibration element configured to receive light from the light emitting component and to produce an output based on the received light, wherein a brightness of the light emitting component is controlled based on the output of the calibration element.

7. The component of claim 4, wherein at least one of the light emitting component and the sensing element comprises a plasma-treated super-hydrophilic surface.

8. The component of claim 4, wherein the sensing element comprises an array of sensing sub-elements, wherein each sensing sub-element is tuned to detect a change of a property of a part of the first substrate.

\* \* \* \* \*